United States Patent
Johnson et al.

(10) Patent No.: US 8,350,037 B2
(45) Date of Patent: *Jan. 8, 2013

(54) THIENO-PYRIDINE DERIVATIVES AS MEK INHIBITORS

(75) Inventors: James Andrew Johnson, Slough (GB); Daniel Christopher Brookings, Slough (GB); Martin Clive Hutchings, Slough (GB); Barry John Langham, Slough (GB); Judi Charlotte Neuss, Slough (GB)

(73) Assignee: UCB Pharma, S.A., Brussels (BE)

( * ) Notice: Subject to any disclaimer, the term of this patent is extended or adjusted under 35 U.S.C. 154(b) by 236 days.

This patent is subject to a terminal disclaimer.

(21) Appl. No.: 12/691,842

(22) Filed: Jan. 22, 2010

(65) Prior Publication Data

US 2010/0179124 A1 Jul. 15, 2010

(30) Foreign Application Priority Data

Jul. 23, 2007 (GB) .................................. 0714384.5
Jul. 16, 2008 (WO) ................ PCT/GB2008/002430

(51) Int. Cl.
*A61K 31/4436* (2006.01)
*C07D 513/04* (2006.01)

(52) U.S. Cl. ...................................... 546/114; 514/301

(58) Field of Classification Search .................. 546/114; 514/301

See application file for complete search history.

(56) References Cited

U.S. PATENT DOCUMENTS

| | | | |
|---|---|---|---|
| 2003/0220365 A1 | 11/2003 | Stewart et al. | |
| 2004/0138251 A1 | 7/2004 | Boschelli et al. | |
| 2005/0049276 A1 | 3/2005 | Kaufman | |
| 2005/0227959 A1 | 10/2005 | Yoshida | |
| 2007/0049603 A1* | 3/2007 | Miknis et al. ............ | 514/252.18 |
| 2009/0149437 A1 | 6/2009 | Hutchings | |
| 2009/0264411 A1 | 10/2009 | Laing | |
| 2011/0021558 A1 | 1/2011 | Brookings | |
| 2011/0172191 A1 | 7/2011 | Johnson | |

FOREIGN PATENT DOCUMENTS

| WO | 02/06213 | 1/2002 |
|---|---|---|
| WO | 03/077855 | 9/2003 |
| WO | 03/077914 | 9/2003 |
| WO | 2004/000846 | 12/2003 |
| WO | 2004/113348 | 12/2004 |
| WO | WO 2004/113347 | 12/2004 |
| WO | 2005/009975 | 2/2005 |
| WO | 2005/023251 | 3/2005 |
| WO | 2005/023818 | 3/2005 |
| WO | WO 2005/023759 | 3/2005 |
| WO | 2005/051906 | 6/2005 |
| WO | WO 2005/051300 | 6/2005 |
| WO | 2007/044515 | 4/2007 |
| WO | 2007/088345 | 8/2007 |
| WO | WO 2007/120101 | 10/2007 |
| WO | 2008/020206 | 2/2008 |

OTHER PUBLICATIONS

West, Anthony R., Solid State Chemistry and its Applications, Wiley, New York, 1988, pp. 358 & 365.*
Wermuth, Camille G. "Molecular Variation Based on Isosteric Replacements" in Chapter 13, The Practice of Medicinal Chemistry, Academic: 1996, pp. 203-237.*
Hamdouchi et. al. "Structure-based design of a new class of highly selective aminoimidazo[1,2-a]pyridine-based inhibitors of cyclin dependent kinases" Bioorganic & Medicinal Chemistry Letters 15 (2005) 1943-1947.*
U.S. Appl. No. 12/182,931, filed Jul. 30, 2008, Martin Clive Hutchings.
Bremner, D.H. et al: "The synthesis of thienopyridines from ortho-halogenated pyridine derivatives. Part 3" Sythesis, (8), 1095-1097 CODEN: SYNTBF; ISSN: 0039-7881, 1998 XP002434659 p. 1095; compound 12 p. 1096; compound 18.
Erian, Ayman Wahba et al: "An Easy Direct Conversion of Pyridine- and Pyrimidinethiones into Multi-Fused Heterocyclic Compounds" Bulletin of the Chemical Society of Japan, 71(10), 2387-2391 CODEN: BCSJA8; ISSN: 0009-2673, 1998, XP002434660 p. 2387; compound 7B.
Bremner, D.H. et al, Synthesis, 1997, 949.
Byrn et al., Solid-State Chemistry of Drugs, $2^{nd}$ Ed., SSCI, Inc., West Lafayette, IN, Ch. 11, 1991, pp. 233-247.
Klemm L. H. et al., "Chemistry of Thienopyridines. XVII. Direct Halogenation of Thieno [2,3-b] pyridine (1)," *Journal of Heterocyclic Chemistry*, 1974, pp. 205-209.
Written Opinion of the International Searching Authority published Jul. 31, 2008 for PCT/GB2007/000310 filed Jan. 30, 2007.
Written Opinion of the International Searching Authority published Feb. 15, 2009 for PCT/GB2007/003114 filed Aug. 15, 2007.
Written Opinion of the International Searching Authority published Jan. 23, 2010 for PCT/GB2008/002430 filed Jul. 16, 2008.
Written Opinion of the International Searching Authority published Jul. 21, 2010 for PCT/GB2009/000144 filed Jan. 20, 2009.
Written Opinion of the International Searching Authority published Dec. 19, 2010 for PCT/GB2009/001504 filed Jun. 12, 2009.
International Search Report mailed Jun. 14, 2007 for PCT/GB2007/000310 filed Jan. 30, 2007.
International Search Report mailed Feb. 29, 2008 for PCT/GB2007/003114 filed Aug. 15, 2007.
International Search Report mailed Aug. 28, 2008 for PCT/GB2008/002430 filed Jul. 16, 2008.
International Search Report mailed May 27, 2009 for PCT/GB2009/000144 filed Jan. 20, 2009.

(Continued)

*Primary Examiner* — David K O'Dell
(74) *Attorney, Agent, or Firm* — Feldman Gale, P.A.; Walter C. Frank

(57) ABSTRACT

A series of thieno[2,3-b]pyridine derivatives which are substituted in the 2-position by a substituted anilino moiety, being selective inhibitors of human MEK (MAPKK) enzymes, are accordingly of benefit in medicine, for example in the treatment of inflammatory, autoimmune, cardiovascular, proliferative (including oncological) and nociceptive conditions.

8 Claims, No Drawings

OTHER PUBLICATIONS

International Search Report mailed Aug. 8, 2009 for PCT/GB2009/001504 filed Jun. 12, 2009.
International Preliminary Report on Patentability issued Aug. 5, 2008 for PCT/GB2007/000310 filed Jan. 30, 2007.
International Preliminary Report on Patentability issued Feb. 17, 2009 for PCT/GB2007/003114 filed Aug. 15, 2007.
International Preliminary Report on Patentability issued Jan. 26, 2010 PCT/GB2008/002430 filed Jul. 16, 2008.
International Preliminary Report on Patentability issued Jul. 27, 2010 for PCT/GB2009/000144 filed Jan. 20, 2009.
International Preliminary Report on Patentability issued Dec. 21, 2010 for PCT/GB2009/001504 filed Jun. 12, 2009.

* cited by examiner

THIENO-PYRIDINE DERIVATIVES AS MEK INHIBITORS

CROSS-REFERENCE TO RELATED APPLICATIONS

The present application is a continuation of International Application No. PCT/GB2008/002430, filed Jul. 16, 2008, which claims priority under 119(a-d) to Great Britain Application No. GB 0714384.5, filed Jul. 23, 2007. Each of these applications is hereby incorporated herein by reference in their entireties.

The present invention relates to a class of thieno-pyridine derivatives and to their use in therapy. More particularly, the invention is concerned with thieno[2,3-b]pyridine derivatives which are substituted in the 2-position by a substituted anilino moiety. These compounds are selective inhibitors of MEK (MAPKK) enzymes, and are accordingly of benefit as pharmaceutical agents, especially in the treatment of adverse inflammatory, autoimmune, cardiovascular, proliferative (including oncological) and nociceptive conditions.

MEK enzymes are implicated in a variety of physiological and pathological functions that are believed to be operative in a range of human diseases. These functions are summarised in paragraphs [0004] and [0005] of US 2005/0049276 A1.

The compounds of use in the present invention, being potent and selective MEK inhibitors, are therefore beneficial in the treatment and/or prevention of various human ailments. These include autoimmune and inflammatory disorders such as rheumatoid arthritis, osteoarthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); proliferative disorders such as restenosis, and oncological conditions including leukaemia, glioblastoma, lymphoma, melanoma, and human cancers of the liver, bone, skin, brain, pancreas, lung, breast, stomach, colon, rectum, prostate, ovary and cervix; and pain and nociceptive disorders, including chronic pain and neuropathic pain.

In addition, the compounds of use in the present invention may be beneficial as pharmacological standards for use in the development of new biological tests and in the search for new pharmacological agents. Thus, the compounds of use in this invention may be useful as radioligands in assays for detecting compounds capable of binding to human MEK enzymes.

MEK inhibitors based on a fused bicyclic aromatic ring system attached to a substituted anilino moiety are known from the art. Examples of relevant publications include WO 2005/051906, WO 2005/023251, US-A-2005/0049276, WO 2005/009975, WO 03/077914 and WO 03/077855.

WO 2005/023818 describes a broad-ranging class of compounds based on a fused bicyclic aromatic ring system, which generically encompasses thieno-pyridine derivatives attached to a substituted anilino moiety but nowhere specifically discloses any precise compound of this type. No discrete pharmacological activity, in terms of an identifiable pharmacological mechanism, is ascribed to the compounds described therein, but they are nevertheless stated to be useful inter alia in the treatment of cell proliferative diseases such as cancer. US-A-2003/0220365 is also of relevance in a related context.

Nowhere in the prior art publications acknowledged above, however, is there the precise disclosure of a class of thieno[2,3-b]pyridine derivatives attached at the 2-position to a substituted anilino moiety. It has now been found that such compounds are particularly valuable as selective inhibitors of MEK enzymes.

The compounds of the present invention are potent and selective MEK inhibitors having a binding affinity ($IC_{50}$) for the human MEK1 and/or MEK2 enzyme of 50 µM or less, generally of 20 µM or less, usually of 5 µM or less, typically of 1 µM or less, suitably of 500 nM or less, ideally of 100 nM or less, and preferably of 20 nM or less (the skilled person will appreciate that a lower $IC_{50}$ FIGURE denotes a more active compound). The compounds of the invention may possess at least a 10-fold selective affinity, typically at least a 20-fold selective affinity, suitably at least a 50-fold selective affinity, and ideally at least a 100-fold selective affinity, for the human MEK1 and/or MEK2 enzyme relative to other human kinases.

The present invention provides a compound of formula (I), or a pharmaceutically acceptable salt, solvate or N-oxide thereof:

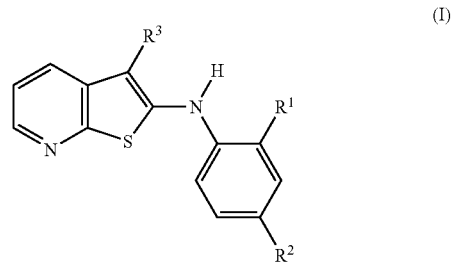

(I)

wherein:

$R^1$ represents hydrogen, halogen or $C_{1-6}$ alkyl;

$R^2$ represents halogen or $C_{1-6}$ alkyl;

$R^3$ represents —$SO_3H$, —$COR^a$, —$SO_2NR^bR^c$ or —$CON(R^d)SO_2R^e$; or $R^3$ represents an optionally substituted five-membered heteroaromatic moiety selected from furyl, thienyl, pyrrolyl, pyrazolyl, oxazolyl, isoxazolyl, thiazolyl, isothiazolyl, imidazolyl, oxadiazolyl, thiadiazolyl, triazolyl and tetrazolyl; or $R^3$ represents an optionally substituted six-membered heteroaromatic ring selected from pyridinyl, pyridazinyl, pyrimidinyl, pyrazinyl and triazinyl;

$R^a$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, C-linked $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents;

$R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents; and $R^c$ represents hydrogen or $C_{1-6}$ alkyl (optionally substituted by hydroxy); or $R^b$ and $R^c$, when taken together with the nitrogen atom to which they are both attached, represent azetidinyl, pyrrolidinyl, piperidinyl, morpholinyl, thiomorpholinyl, piperazinyl, homopiperidinyl, homomorpholinyl or homopiperazinyl, any of which groups may be optionally substituted by one or more substituents;

$R^d$ represents hydrogen or $C_{1-6}$ alkyl; and $R^e$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents.

Co-pending international patent application no. PCT/GB2007/000310, published on 9 Aug. 2007 as WO 2007/088345, describes a class of compounds of formula (I) as depicted above, and pharmaceutically acceptable salts, solvates and N-oxides thereof, as MEK inhibitors. Substituent $R^3$ as defined therein, however, differs in all respects from substituent $R^3$ as defined above.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl and 2,2-dimethylpropyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Specific $C_{3-7}$ cycloalkyl groups are cyclopropyl, cyclobutyl, cyclopentyl, cyclohexyl and cycloheptyl.

Suitable aryl groups include phenyl and naphthyl, preferably phenyl.

Suitable aryl($C_{1-6}$)alkyl groups include benzyl, phenylethyl, phenylpropyl and naphthylmethyl.

Suitable heterocycloalkyl groups, which may comprise benzo-fused analogues thereof, include azetidinyl, tetrahydrofuranyl, dioxolanyl, pyrrolidinyl, indolinyl, imidazolidinyl, tetrahydropyranyl, piperidinyl, 1,2,3,4-tetrahydroquinolinyl, 1,2,3,4-tetrahydroisoquinolinyl, piperazinyl, morpholinyl and thiomorpholinyl.

Suitable heteroaryl groups include furyl, benzofuryl, dibenzofuryl, thienyl, benzothienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl, pyridinyl, quinolinyl, isoquinolinyl, pyridazinyl, pyrimidinyl, pyrazinyl and triazinyl groups.

The term "halogen" as used herein is intended to include fluorine, chlorine, bromine and iodine atoms.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C$=O)-enol ($CH$=$CHOH$) tautomers. Formula (I) and the formulae depicted hereinafter are intended to represent all individual tautomers and all possible mixtures thereof, unless stated or shown otherwise.

In one embodiment, $R^1$ represents hydrogen. In another embodiment, $R^1$ represents halogen, particularly fluoro or chloro, especially fluoro. In a further embodiment, $R^1$ represents $C_{1-6}$ alkyl, especially methyl.

Typically, $R^1$ is fluoro.

In one embodiment, $R^2$ represents halogen, especially bromo or iodo. In another embodiment, $R^2$ represents $C_{1-6}$ alkyl, especially methyl.

In one specific embodiment, $R^2$ is bromo. In another specific embodiment, $R^2$ is iodo.

Suitably, the group $R^a$, $R^b$ or $R^e$, or the cyclic moiety —$NR^bR^c$, may be unsubstituted, or substituted by one or more substituents, typically by one or two substituents. In one embodiment, the group $R^a$, $R^b$ or $R^e$, or the cyclic moiety —$NR^bR^c$, is unsubstituted. In another embodiment, the group $R^a$, $R^b$ or $R^e$, or the cyclic moiety —$NR^bR^c$, is monosubstituted. In a further embodiment, the group $R^a$, $R^b$ or $R^e$, or the cyclic moiety —$NR^bR^c$, is disubstituted.

Examples of typical substituents on $R^a$, $R^b$ or $R^e$, or on the cyclic moiety —$NR^bR^c$, include $C_{1-6}$ alkyl, hydroxy, hydroxy($C_{1-6}$)alkyl, $C_{1-6}$ alkoxy, $C_{1-6}$ alkoxy($C_{1-6}$)alkyl, amino($C_{1-6}$)alkyl, (amino)(hydroxy)($C_{1-6}$)alkyl, halogen, oxo, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, di($C_{1-6}$)alkyl-hydrazinylcarbonyl, amino, $C_{1-6}$ alkylamino, di($C_{1-6}$)alkylamino, $C_{2-6}$ alkylcarbonylamino, $C_{2-6}$ alkoxycarbonylamino, $C_{2-6}$ alkoxycarbonylamino($C_{1-6}$)alkyl, $C_{2-6}$ alkoxycarbonyl-($C_{1-6}$)alkylamino($C_{1-6}$)alkyl, aminocarbonylamino, aminocarbonyl, $C_{1-6}$ alkylamino-carbonyl, di($C_{1-6}$)alkylaminocarbonyl, aminosulfonyl, $C_{1-6}$ alkylsulfonyl and $C_{1-6}$ alkylaminocarbonyl($C_{1-6}$)alkyl. A further example of a typical substituent is carboxy-($C_{1-6}$)alkylamino($C_{1-6}$)alkyl.

Examples of particular substituents on $R^a$, $R^b$ or $R^e$, or on the cyclic moiety —$NR^bR^c$, include methyl, hydroxy, hydroxymethyl, 2-hydroxyethyl, methoxy, methoxy-methyl, aminomethyl, 2-amino-3-hydroxypropyl, fluoro, oxo, acetyl, carboxy, carboxy-methyl, methoxycarbonyl, ethoxycarbonyl, tert-butoxycarbonyl, ethoxycarbonylmethyl, dimethylhydrazinylcarbonyl, amino, methylamino, 1,3-dimethylbutylamino, dimethylamino, acetylamino, tert-butoxycarbonylamino, tert-butoxycarbonylaminomethyl, ethoxycarbonylmethylaminomethyl, ethoxycarbonylethylaminomethyl, aminocarbonyl-amino, aminocarbonyl, ethylaminocarbonyl, diethylaminocarbonyl, aminosulfonyl, methylsulfonyl and methylaminocarbonylmethyl. A further example of a particular substituent is carboxyethylaminomethyl.

Definitive examples of favoured substituents on $R^a$, $R^b$ or $R^e$, or on the cyclic moiety —$NR^bR^c$, include hydroxy, amino, amino($C_{1-6}$)alkyl, $C_{2-6}$ alkoxycarbonylamino, carboxy($C_{1-6}$)alkylamino($C_{1-6}$)alkyl and $C_{2-6}$ alkoxycarbonyl($C_{1-6}$)alkylamino($C_{1-6}$)alkyl.

Examples of favoured substituents on $R^a$, $R^b$ or $R^e$, or on the cyclic moiety —$NR^bR^c$, include hydroxy, amino, amino ($C_{1-6}$)alkyl, $C_{2-6}$ alkoxycarbonylamino and $C_{2-6}$ alkoxycarbonyl($C_{1-6}$)alkylamino($C_{1-6}$)alkyl.

Definitive examples of specific substituents on $R^a$, $R^b$ or $R^e$, or on the cyclic moiety —$NR^bR^c$, include hydroxy, amino, aminomethyl, tert-butoxycarbonylamino, carboxyethylaminomethyl, ethoxycarbonylmethylaminomethyl and ethoxycarbonylethyl-aminomethyl.

Examples of specific substituents on $R^a$, $R^b$ or $R^e$, or on the cyclic moiety —$NR^bR^c$, include hydroxy, amino, aminomethyl, tert-butoxycarbonylamino, ethoxycarbonylmethylaminomethyl and ethoxycarbonylethylaminomethyl.

Favourably, $R^a$ represents $C_{1-6}$ alkyl, C-linked $C_{3-7}$ heterocycloalkyl, or heteroaryl, any of which groups may be optionally substituted by one or more substituents.

Suitably, $R^a$ represents $C_{1-6}$ alkyl or $C_{3-7}$ cycloalkyl, either of which groups may be optionally substituted by one or more substituents. Suitable substituents on $R^a$ include hydroxy and amino.

In one embodiment, $R^a$ represents $C_{1-6}$ alkyl, suitably methyl or ethyl, and especially methyl. In another embodiment, $R^a$ represents $C_{3-7}$ cycloalkyl, especially cyclobutyl.

In a further embodiment, $R^a$ represents substituted or unsubstituted C-linked $C_{3-7}$ heterocycloalkyl. Particular examples thereof include azetidin-2-yl, azetidin-3-yl, pyrrolidin-2-yl, pyrrolidin-3-yl, piperidin-2-yl, piperidin-3-yl, piperidin-4-yl, piperazin-2-yl, morpholin-2-yl and morpholin-3-yl. Specific examples thereof include azetidin-3-yl, pyrrolidin-2-yl and piperidin-4-yl.

In a still further embodiment, $R^a$ represents substituted or unsubstituted heteroaryl. Particular examples thereof include pyridin-2-yl, pyridin-3-yl and pyridin-4-yl, especially pyridin-4-yl.

Favourably, $R^b$ represents hydrogen; or $C_{1-6}$ alkyl, $C_{3-7}$ cycloalkyl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Favoured values of $R^b$ include hydrogen, methyl, ethyl, propyl, cyclopropyl-methyl, azetidinyl, pyrrolidinyl, piperidinyl, azetidinylmethyl, dioxolanylmethyl, pyrrolidinylmethyl, morpholinylethyl and morpholinylpropyl, any of which groups may be optionally substituted by one or more substituents. Favoured substituents in this context include $C_{1-6}$ alkyl (especially methyl), hydroxy, amino, $C_{2-6}$ alkoxycarbonyl (especially tert-butoxycarbonyl) and di($C_{1-6}$)alkylamino (especially dimethylamino).

Specific values of $R^b$ include hydrogen, methyl, 2-hydroxyethyl, 3-hydroxypropyl, 2,3-dihydroxypropyl, isopropyl, 1-hydroxyprop-2-yl, 2-amino-2-methylpropyl, 2,2-dimethyl-3-(dimethylamino)propyl, cyclopropylmethyl, 1-tert-butoxycarbonylazetidin-3-yl, pyrrolidin-3-yl, 1-tert-butoxycarbonylpyrrolidin-3-yl, piperidin-3-yl, piperidin-4-yl, 1-methylpiperidin-4-yl, 1-tert-butoxycarbonylpiperidin-3-yl, 1-tert-butoxycarbonyl-piperidin-4-yl, 1-tert-butoxycarbonylazetidin-3-ylmethyl, 2,2-dimethyl-[1,3]dioxolan-4-ylmethyl, pyrrolidin-2-ylmethyl, 2-(morpholin-4-yl)ethyl and 3-(morpholin-4-yl)propyl.

Typically, $R^b$ represents $C_{1-6}$ alkyl, optionally substituted by one or more, preferably one or two, hydroxy groups.

Typical values of $R^b$ include methyl, hydroxyethyl, hydroxypropyl, dihydroxypropyl and isopropyl. In one embodiment, $R^b$ represents methyl. In another embodiment, $R^b$ represents hydroxyethyl, especially 2-hydroxyethyl. In a further embodiment, $R^b$ represents hydroxypropyl, especially 3-hydroxypropyl. In a still further embodiment, $R^b$ represents dihydroxypropyl, especially 2,3-dihydroxypropyl. In an additional embodiment, $R^b$ represents isopropyl.

In one embodiment, $R^c$ is hydrogen. In another embodiment, $R^c$ represents $C_{1-6}$ alkyl, especially methyl or isopropyl, particularly isopropyl. In a further embodiment, $R^c$ represents hydroxy($C_{1-6}$)alkyl, e.g. hydroxyethyl (especially 2-hydroxyethyl).

Alternatively, the moiety —$NR^bR^c$ may suitably represent azetidin-1-yl, pyrrolidin-1-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Particular values for the cyclic moiety —$NR^bR^c$ include azetidin-1-yl, pyrrolidin-1-yl and piperazin-1-yl, any of which groups may be optionally substituted by one or more substituents.

Specific values of the cyclic moiety —$NR^bR^c$ include 3-hydroxyazetidin-1-yl, 3-aminoazetidin-1-yl, 3-(aminomethyl)azetidin-1-yl, 3-(aminomethyl)-3-hydroxyazetidin-1-yl, 3-(tert-butoxycarbonylamino)azetidin-1-yl, 3-(ethoxycarbonylmethylaminomethyl)-azetidin-1-yl, 3-(ethoxycarbonylethylaminomethyl)azetidin-1-yl, pyrrolidin-1-yl, 3-hydroxypyrrolidin-1-yl, 3-aminopyrrolidin-1-yl, 3-(tert-butoxycarbonylamino)-pyrrolidin-1-yl and piperazin-1-yl. A further specific value for the cyclic moiety —$NR^bR^c$ is 3-(carboxyethylaminomethyl)azetidin-1-yl.

In one embodiment, $R^d$ represents hydrogen. In another embodiment, $R^d$ represents $C_{1-6}$ alkyl, suitably methyl or ethyl, and especially methyl.

Favourably, $R^e$ represents hydrogen or trifluoromethyl; or $C_{1-6}$ alkyl, $C_{3-7}$ cycloalkyl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

In a specific embodiment, $R^e$ represents trifluoromethyl.

In a first embodiment, $R^3$ represents —$SO_3H$. In a second embodiment, $R^3$ represents —$COR^a$, in which $R^a$ is as defined above. In a third embodiment, $R^3$ represents —$SO_2NR^bR^c$, in which $R^b$ and $R^c$ are as defined above. In a fourth embodiment, $R^3$ represents —$CON(R^d)SO_2R^e$, in which $R^d$ and $R^e$ are as defined above. In a fifth embodiment, $R^3$ represents an optionally substituted five-membered heteroaromatic moiety selected from furyl, thienyl, pyrrolyl, pyrazolyl, oxazolyl, isoxazolyl, thiazolyl, isothiazolyl, imidazolyl, oxadiazolyl, thiadiazolyl, triazolyl and tetrazolyl. In a sixth embodiment, $R^3$ represents an optionally substituted six-membered heteroaromatic ring selected from pyridinyl, pyridazinyl, pyrimidinyl, pyrazinyl and triazinyl.

Where $R^3$ in the compounds of formula (I) above represents a five-membered or six-membered heteroaromatic ring, this ring may be unsubstituted, or may suitably be substituted by one or, where possible, two substituents. In one embodiment, this ring is unsubstituted. In another embodiment, this ring is monosubstituted. In a further embodiment, this ring is disubstituted. As will be appreciated, where $R^3$ represents an oxadiazolyl, thiadiazolyl or tetrazolyl moiety, only one substituent will be possible; otherwise, one or two optional substituents may be accommodated around the five-membered or six-membered heteroaromatic moiety $R^3$. Examples of typical substituents on the five-membered or six-membered heteroaromatic moiety as specified for $R^3$ include $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano and trifluoromethyl. Examples of suitable substituents include $C_{1-6}$ alkyl and aryl.

When the group $R^3$ represents an optionally substituted five-membered heteroaromatic moiety, this is typically an oxadiazolyl (especially 1,3,4-oxadiazolyl) or tetrazolyl moiety. Particular values include 5-methyl-1,3,4-oxadiazol-2-yl, 5-phenyl-1,3,4-oxadiazol-2-yl and tetrazol-5-yl.

When the group $R^3$ represents an optionally substituted six-membered heteroaromatic moiety, this will be a pyridinyl, pyridazinyl, pyrimidinyl, pyrazinyl, 1,2,3-triazinyl, 1,2,4-triazinyl or 1,3,5-triazinyl moiety.

A particular sub-group of compounds according to the invention is represented by the compounds of formula (II), and pharmaceutically acceptable salts, solvates and N-oxides thereof:

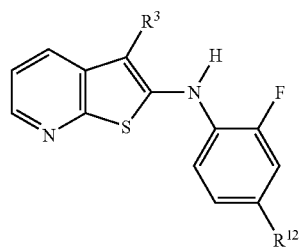

(II)

wherein:
$R^{12}$ represents halogen; and
$R^3$ is as defined above.

In one specific embodiment, $R^{12}$ is bromo. In another specific embodiment, $R^{12}$ is iodo.

Specific novel compounds in accordance with the present invention include each of the compounds whose preparation is described in the accompanying Examples, and pharmaceutically acceptable salts and solvates thereof.

The present invention also provides a pharmaceutical composition which comprises a compound of formula (I) as defined above, or a pharmaceutically acceptable salt, solvate or N-oxide thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above wherein $R^3$ represents —$SO_2NR^bR^c$ may be prepared by a process which comprises reacting a compound of formula H—$NR^bR^c$ with a compound of formula (III):

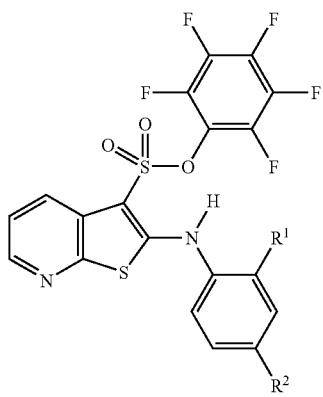
(III)

wherein $R^1$ and $R^2$ are as defined above.

The reaction is conveniently effected in a suitable solvent, e.g. dichloromethane, typically under basic conditions, e.g. in the presence of an organic base such as pyridine or triethylamine.

The intermediates of formula (III) may suitably be prepared by reacting a compound of formula (IV):

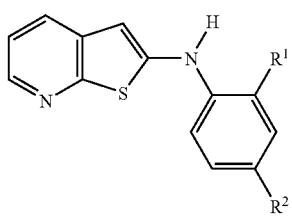
(IV)

wherein $R^1$ and $R^2$ are as defined above; with chlorosulphonic acid; followed by treatment with pentafluorophenol, typically in the presence of an organic base such as pyridine.

In an alternative procedure, the compounds of formula (I) above wherein $R^3$ represents —$SO_2NR^bR^c$ may be prepared by a process which comprises reacting a compound of formula (IV) as defined above with chlorosulphonic acid; followed by treatment with a compound of formula H—$NR^bR^c$. The reaction is conveniently effected in an inert solvent, e.g. dichloromethane.

The intermediates of formula (IV) may suitably be prepared by decarboxylating a compound of formula (V):

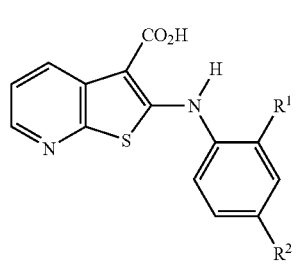
(V)

wherein $R^1$ and $R^2$ are as defined above.

Decarboxylation is conveniently effected by heating compound (V), typically at the reflux temperature, in an inert solvent such as toluene.

The intermediates of formula (V) above may suitably be prepared by reacting a compound of formula (VI) with a compound of formula (VII):

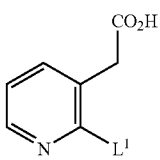
(VI)

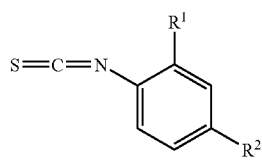
(VII)

wherein $R^1$ and $R^2$ are as defined above, and $L^1$ represents a suitable leaving group.

The leaving group $L^1$ is typically a halogen atom, e.g. chloro.

The reaction is conveniently effected, at an elevated temperature if necessary, in a suitable solvent, e.g. tetrahydrofuran, typically under basic conditions, e.g. in the presence of lithium diisopropylamide.

The intermediates of formula (VII) above may be prepared by reacting a compound of formula (VIII):

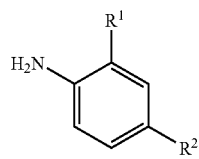
(VIII)

wherein $R^1$ and $R^2$ are as defined above; with thiophosgene.

The reaction is conveniently effected in a suitable solvent, typically a mixture of chloroform and water.

In another procedure, the compounds of formula (I) above wherein $R^3$ represents —$COR^a$ may be prepared by a process which comprises reacting a compound of formula (VII) as defined above with a compound of formula (IX):

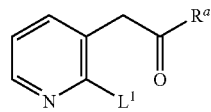
(IX)

wherein $R^a$ and $L^1$ are as defined above.

The reaction is conveniently effected, at an elevated temperature if necessary, in a suitable solvent, e.g. dimethylsulphoxide, typically under basic conditions, e.g. in the presence of an inorganic base such as sodium hydride.

Alternatively, the compounds of formula (I) above wherein $R^3$ represents —$COR^a$ may be prepared by reacting a compound of formula (X):

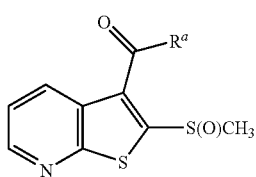

wherein $R^a$ is as defined above; with a compound of formula (VIII) as defined above.

The reaction may conveniently be effected by treating compound (VIII) with a base, e.g. lithium bis(trimethylsilyl) amide, in a suitable solvent, e.g. tetrahydrofuran, followed by the addition of compound (X).

The intermediates of formula (X) above may be prepared from a compound of formula (XI):

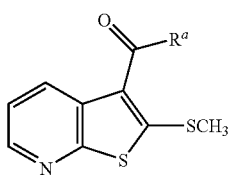

wherein $R^a$ is as defined above; by oxidation of the methylsulfanyl group.

The reaction may conveniently be effected by treatment with a suitable oxidising agent, e.g. Oxone® (potassium peroxymonosulfate), in an appropriate solvent, e.g. aqueous methanol.

The intermediates of formula (XI) above may be prepared from a compound of formula (XII):

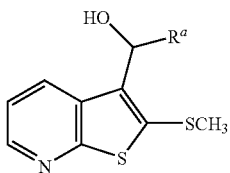

wherein $R^a$ is as defined above; by oxidation of the hydroxy group.

The reaction may conveniently be effected by treatment with a suitable oxidising agent, e.g. Dess-Martin periodinane, in an appropriate solvent, e.g. a chlorinated solvent such as dichloromethane.

The intermediates of formula (XII) above may be prepared by reacting a compound of formula $R^a$—CHO with the compound of formula (XIII):

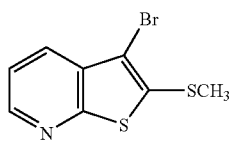

wherein $R^a$ is as defined above.

The reaction may conveniently be effected by treating compound (XIII) with a base, e.g. n-butyllithium, in a suitable solvent, e.g. tetrahydrofuran, followed by addition of the compound of formula $R^a$—CHO.

In a further procedure, the compounds of formula (I) above wherein $R^3$ represents —$SO_3H$ may be prepared by a process which comprises reacting a compound of formula (IV) as defined above with chlorosulphonic acid; followed by treatment with a base, e.g. an organic base such as N,N-diisopropylethylamine. The reaction is conveniently effected in an inert solvent, e.g. dichloromethane.

In an additional procedure, the compounds of formula (I) above wherein $R^3$ represents —$CON(R^d)SO_2R^e$ may be prepared by a process which comprises reacting a compound of formula (V) as defined above with a compound of formula $HN(R^d)SO_2R^e$ in the presence of a condensing agent. A suitable condensing agent is 1-(3-dimethylamino-propyl)-3-carbodiimide hydrochloride (EDC), in which case the reaction is conveniently effected in the presence of 4-(dimethylamino)pyridine.

The compounds of formula (I) above wherein $R^3$ represents a 5-substituted 1,3,4-oxadiazol-2-yl moiety may be prepared by a process which comprises reacting a compound of formula (V) as defined above with the appropriate hydrazide, e.g. a $C_{2-6}$ acylhydrazide such as N-acetylhydrazide, or an aroyl hydrazide such as benzoic hydrazide, typically in the presence of a condensing agent such as (bromo)tris-(pyrrolidino)phosphonium hexafluorophosphate (PyBrOP) and a base, e.g. an organic base such as N,N-diisopropylethylamine; followed by cyclisation of the carbohydrazide intermediate thereby obtained by treatment with a reagent such as phosphorus oxychloride, typically at an elevated temperature.

The compounds of formula (I) above wherein $R^3$ represents a tetrazol-5-yl moiety may be prepared by a process which comprises reacting a compound of formula (XIV):

wherein $R^1$ and $R^2$ are as defined above; with an azide, e.g. an alkali metal azide such as sodium azide.

The reaction is conveniently effected at an elevated temperature in a suitable solvent, e.g. a dipolar aprotic solvent such as N,N-dimethylformamide.

The intermediates of formula (XIV) above may suitably be prepared by reacting a compound of formula (VII) as defined above with a compound of formula (XV):

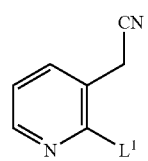

wherein $L^1$ is as defined above; under conditions analogous to those described above for the reaction between compounds (VII) and (IX).

Where they are not commercially available, the starting materials of formula (VI), (VIII), (IX), (XIII) and (XV) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) wherein $R^3$ contains a nitrogen atom to which a tert-butoxy-carbonyl (BOC) group is attached may be converted into the corresponding compound wherein $R^3$ contains an N—H functionality by treatment with an acid, e.g. a mineral acid such as hydrochloric acid, or an organic acid such as trifluoroacetic acid. A compound of formula (I) wherein $R^3$ contains a nitrogen atom to which a benzyloxycarbonyl group is attached may be converted into the corresponding compound wherein $R^3$ contains an N—H functionality by treatment with trifluoroacetic acid. A compound of formula (I) wherein $R^3$ contains an N—H functionality may be converted into the corresponding compound wherein $R^3$ contains a nitrogen atom to which an ethoxycarbonylmethyl group is attached by treatment with ethyl chloroacetate or ethyl bromoacetate, typically in the presence of an organic base such as triethylamine or N,N-diisopropylethylamine; the resulting compound may then be converted into the corresponding compound wherein $R^3$ contains a nitrogen atom to which a carboxymethyl group is attached by treatment with an alkaline reagent such as sodium hydroxide, typically in an aqueous solution of a lower alkanol such as ethanol. A compound of formula (I) wherein $R^3$ contains an N—H functionality may be converted into the corresponding compound wherein $R^3$ contains a nitrogen atom to which an ethoxycarbonylethyl group is attached by treatment with ethyl acrylate, typically in the presence of an organic base such as N,N-diisopropylethylamine. In general, a compound of formula (I) wherein $R^3$ contains an ester moiety, e.g. a $C_{1-6}$ alkoxycarbonyl group such as methoxycarbonyl or ethoxycarbonyl, may be converted into the corresponding compound wherein $R^3$ contains a carboxy (—$CO_2H$) moiety by treatment with an alkali metal hydroxide, e.g. sodium hydroxide or lithium hydroxide. A compound of formula (I) wherein $R^3$ contains a 2,2-dimethyl-[1,3]dioxolan-4-ylmethyl moiety may be converted into the corresponding compound wherein $R^3$ contains a 2,3-dihydroxypropyl moiety by treatment with a mineral acid such as hydrochloric acid. The pyridine-N-oxide derivative of a compound of formula (I) may be converted into the corresponding compound of formula (I) by treatment with triphenyl phosphine and phosphorus trichloride.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, $3^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human MEK enzyme.

In Vitro MEK Assay

MEK1 activity was measured in a cascade assay initiated by active Raf, via activation of MEK, Erk2 and subsequent phosphorylation of fluorescein-labelled Erk-tide substrate in an assay based on fluorescence polarisation (IMAP). The assay was carried out in 20 mM Tris+5 mM $MgCl_2$+2 mM DL-dithiothreitol+0.01% Tween 20 pH 7.2, containing 1.5 nM unactive MEK, 100 nM unactive Erk and 200 nM Erk-tide (all concentrations are final concentrations). Compounds, or DMSO controls, were tested at a final concentration of 2% DMSO, and the assay initiated in the presence of 5 µM ATP by addition of 1.25 nM active Raf in assay buffer. After 20 min at r.t., stop solution was added followed by IMAP binding beads, the assay mixture was then incubated for 90 min at r.t. (with shaking) and then read on a Molecular Devices LJL HT reader.

When tested in the above assay, the compounds of the accompanying Examples were all found to inhibit human MEK enzyme with $IC_{50}$ values of 10 µM or better.

EXAMPLES

Abbreviations Used

EtOAc—ethyl acetate DMSO—dimethylsulphoxide
THF—tetrahydrofuran DCM—dichloromethane
$Et_2O$/ether—diethyl ether $CDCl_3$—deuterochloroform
MeOH—methanol MeCN—acetonitrile
EtOH—ethanol ES—electrospray
DMF—N,N-dimethylformamide HOBT—1-hydroxybenzotriazole
$SiO_2$—silica NMM—N-methylmorpholine
h—hour(s) min—minute(s)
r.t.—room temperature aq—aqueous
sat.—saturated RT—retention time
conc.—concentrated BOC—tert-butoxycarbonyl TFA—trifluoroacetic acid
EDC—1-(3-dimethylaminopropyl)-3-carbodiimide hydrochloride
PyBrOP—(bromo)tris(pyrrolidino)phosphonium hexafluorophosphate
Dess-Martin periodinane—1,1,1-tris(acetyloxy)-1,1-dihydro-1,2-benziodoxol-3(1H)-one All NMR spectra were obtained either at 300 MHz or 400 MHz.

Compounds were named with the aid of ACD Labs Name (v. 7.0) supplied by Advanced Chemical Development, Toronto, Canada.

Standard LCMS Method

The LC-MS system used comprises a Waters Alliance 2795 HT quaternary HPLC, Waters 996 Photo Diode Array (PDA) detector and Waters ZQ 4000 single quadrupole mass spectrometer. The ZQ can acquire data simultaneously in positive and negative electrospray ionisation modes.

| ZQ Mass Spectrometer | | | |
|---|---|---|---|
| Capillary | 3.5 kV | Cone | 50 V |
| Extractor | 2 V | Source Temp | 80° C. |
| Desolvation Temp | 200° C. | Cone Gas | 150 L/h |
| Desolvation Gas | 250 L/h | Multiplier | 650 V |

Data were acquired in a full scan from 100 to 1000 m/z.

| Scan duration | 0.80 s |
|---|---|
| Interscan delay | 0.20 s |

HPLC

Analytical reverse phase separation was carried out on a Gemini C18 from Phenomenex 50×4.6 mm with 5 μm silica.

| Injection Volume | 5 μL |
|---|---|
| UV data | 240 to 400 nm |
| Sample Temperature | 20° C. |
| Column Temperature | 30° C. |
| Flow Rate | 0.9 mL/min |
| Split to ZQ | ~0.40 mL/min |

Solvent A: 90% 10 mM $NH_4HCO_2$ in water/0.1% formic acid/10% $CH_3CN$
Solvent B: 90% $CH_3CN$/0.1% formic acid/10% 10 mM $NH_4HCO_2$ in water
Solvent C: 90% 10 mM $NH_4HCO_2$ in water/0.1% ammonia/10% $CH_3CN$
Solvent D: 90% $CH_3CN$/10% 10 mM $NH_4HCO_2$ in water/0.1% ammonia Gradient Program
For method 5_95_pH=3

| Time (min) | A % | B % | Flow | Curve |
|---|---|---|---|---|
| 0.00 | 95.0 | 5.0 | 0.900 | 1 |
| 2.00 | 5.0 | 95.0 | 0.900 | 6 |
| 4.00 | 5.0 | 95.0 | 0.900 | 6 |
| 5.00 | 95.0 | 5.0 | 0.900 | 6 |

For method 5_95_pH=10

| Time (min) | A % | B % | Flow | Curve |
|---|---|---|---|---|
| 0.00 | 95.0 | 5.0 | 0.900 | 1 |
| 2.00 | 5.0 | 95.0 | 0.900 | 6 |
| 4.00 | 5.0 | 95.0 | 0.900 | 6 |
| 5.00 | 95.0 | 5.0 | 0.900 | 6 |

Preparative UV-HPLC

The LC system comprises a Waters 2525 quaternary pump, a Waters 996 Photo Diode Array (PDA) detector, a Waters 2700 sample manager, a Column Fluidics Organiser and a Waters Fraction Collector operating in reverse phase at one of two pH systems.

Low pH System (Approximately pH 3.2)

The reverse phase separation was carried out on a Luna C18 from Phenomenex 100×21.2 mm with 5 μm silica.

| Injection Volume | 500 μL |
|---|---|
| UV data | 254 nm |
| Flow Rate | 20 mL/min |
| Solvent A | 90% water/10% $CH_3CN$/0.1% formic acid |
| Solvent B | 90% $CH_3CN$/10% water/0.1% formic acid |

High pH System (approximately pH 9.5)

The reverse phase separation was carried out on a Gemini C18 from Phenomenex 150×21.2 mm with 10 μm silica.

| Injection Volume | 500 μL |
|---|---|
| UV data | 254 nm |
| Flow Rate | 20 mL/min |
| Solvent C | 90% 10 mM $NH_4HCO_2$ in water/0.1% ammonia/10% $CH_3CN$ |
| Solvent D | 90% $CH_3CN$/10% 10 mM $NH_4HCO_2$ in water/0.1% ammonia |

Typical gradient profiles are described below:

Gradient Program for Low pH Method

| Time | A % | B % | C % | D % | Flow | Curve |
|---|---|---|---|---|---|---|
| 0.00 | 95.0 | 5.0 | 0.0 | 0.0 | 20 | 1 |
| 9.00 | 5.0 | 95.0 | 0.0 | 0.0 | 20 | 6 |
| 11.00 | 5.0 | 95.0 | 0.0 | 0.0 | 20 | 6 |
| 11.50 | 95.0 | 5.0 | 0.0 | 0.0 | 20 | 6 |
| 12.00 | 95.0 | 5.0 | 0.0 | 0.0 | 20 | 6 |

Gradient Program for High pH Method

| Time | A % | B % | C % | D % | Flow | Curve |
|---|---|---|---|---|---|---|
| 0.00 | 0.0 | 0.0 | 95.0 | 5.0 | 20 | 1 |
| 9.00 | 0.0 | 0.0 | 5.0 | 95.0 | 20 | 6 |
| 11.00 | 0.0 | 0.0 | 5.0 | 95.0 | 20 | 6 |
| 11.50 | 0.0 | 0.0 | 95.0 | 5.0 | 20 | 6 |
| 12.00 | 0.0 | 0.0 | 95.0 | 5.0 | 20 | 6 |

Intermediate 1

2-Chloro-3-(chloromethyl)pyridine

To a 500 mL, round-bottom, 3-necked flask equipped with dropping funnel and magnetic stirrer and set for reflux was prepared a solution of 2-chloro-3-(hydroxymethyl)-pyridine (25.0 g, 174 mmol) in DCM (250 mL) under positive nitrogen atmosphere. The solution was cooled to 10° C. and thionyl chloride (31.0 g) was added dropwise over 25 minutes (exothermic). The reaction was then heated to reflux for 90 minutes, at which point the reaction was deemed complete by HPLC. The reaction mixture was cooled below boiling point and the equipment set for distillation. A total of 110 mL of DCM was initially removed and replenished with fresh DCM (110 mL), followed by another 80 mL of DCM before cooling the solution to 5-10° C. The acidic mixture was treated with a saturated solution of sodium bicarbonate (3 volumes) to pH 10. The lower organic phase was separated and the aqueous phase extracted with DCM (2 volumes). The organic phases were gathered, dried on sodium sulfate, filtered and concentrated in vacuo to afford the title compound as a pale yellow oil in excellent purity and yield (24.8 g, 88%). $\delta_H$ ($d_6$-DMSO, 300 MHz) 8.45 (1H, dd), 8.10 (1H, dd), 7.50 (1H, dd), 4.85 (2H, s). LCMS (ES)$^+$ RT 3.00 min, m/e 162.1.

Intermediate 2

(2-Chloropyridin-3-yl)acetonitrile

In a 3 L reactor, set for reflux under positive nitrogen pressure and using a bleach scrubber, was prepared a solution of potassium cyanide (68.32 g, 1.04M) in EtOH (136 mL) and water (255 mL). The mixture was heated to reflux, at which point a solution of 2-chloro-3-(chloromethyl)pyridine (Intermediate 1; 170.0 g, 1.04M) in EtOH (170 mL) was added dropwise over 30 minutes. The whole mixture was maintained at reflux for a further 150 minutes. The mixture was then allowed to cool just below boiling point and the equipment set for distillation. A total of 8.5 volumes of EtOH were removed. On cooling, half a volume of water was added. At a temperature of 40° C., the solution was seeded and crystallised instantaneously. The thick beige slurry was allowed to cool to ambient temperature and then to 0° C. This mixture was filtered, rinsed with cold water (2 vols) and dried at 45° C. in a vacuum oven overnight. The title compound was afforded as a beige solid in excellent yield and purity (126.9 g, 80%). $\delta_H$ ($d_6$-DMSO, 300 MHz) 8.45 (1H, dd), 8.00 (1H, dd), 7.50 (1H, dd), 4.15 (2H, s). LCMS (ES)$^+$ RT 2.15 min, m/e 153.01 & 155.01 (M+1 & M+3, Product).

Intermediate 3

(2-Chloropyridin-3-yl)acetic acid

To a 2 L reactor, set for reflux, was stirred a pre-prepared 15% w/w solution of sodium hydroxide (5 vols) to which was added (2-chloropyridin-3-yl)acetonitrile (Intermediate 2; 276.4 g, 1.81M). The beige suspension was heated to reflux for 30 minutes, at which point the reaction was deemed complete by HPLC. The brown solution was then cooled to 0-5° C. and acidified to pH 1 with conc. HCl while keeping the temperature below 10° C., using concentrated hydrochloric acid (1.8 vols). An off-white solid precipitated and was left to mature for another hour before filtration. Once dried, the material was recrystallised from propan-2-ol (4 vols) to afford the title compound as an off-white material in excellent yield and purity (280.3 g, 90%). $\delta_H$ ($d_6$-DMSO, 300 MHz) 12.70 (1H, s), 8.35 (1H, dd), 7.85 (1H, dd), 7.40 (1H, dd), 4.25 (2H, s). LCMS (ES)$^+$ RT 1.75 min, m/e 171.99 (M+1, Product).

Intermediate 4

2-Fluoro-4-iodo-1-isothiocyanatobenzene

Thiophosgene (3.55 ml, 46.4 mmol) was added to a rapidly-stirred mixture of 2-fluoro-4-iodoaniline (10.0 g, 42.2 mmol) in CHCl$_3$ (200 ml) and water (100 ml). The mixture was stirred at r.t. for 16 h. The organic phase was dried (Na$_2$SO$_4$) and concentrated in vacuo to give the title compound as an off-white crystalline solid (11.8 g, quant.). $\delta_H$ (DMSO-$d_6$) 7.87 (1H, dd, J 1.8, 9.5 Hz), 7.63 (1H, ddd, J 1.0, 1.8, 8.4 Hz), 7.25 (1H, dd, J 8.2, 8.4 Hz).

Intermediate 5

2-[(2-Fluoro-4-iodophenyl)amino]thieno[2,3-b]pyridine-3-carboxylic acid

To a stirred solution of diisopropylamine (35.3 mL, 250 mmol) in anhydrous THF (200 mL) cooled to −15° C. was added n-butyllithium (100 mL, 2.5M in hexanes, 250 mmol) slowly such that an internal temperature of between −10 and 0° C. was maintained. The resultant mixture was stirred at room temperature for 15 minutes before being cooled to 0° C. The solution of lithium diisopropylamide was added via cannula to a rapidly stirred suspension of (2-chloropyridin-3-yl) acetic acid (Intermediate 3; 21.4 g, 125 mmol) in anhydrous THF (400 mL) at 0° C. The temperature of the reaction mixture was maintained at 0° C. over the course of the addition. Upon complete addition of the lithium diisopropylamide solution the resultant bright yellow suspension was stirred at 0° C. for 15 minutes. A solution of Intermediate 4 (34.9 g, 125 mmol) in anhydrous THF (200 mL) was then added to the reaction mixture via cannula and the mixture heated to 65° C. for 18 hours. The reaction mixture was cooled and the volatiles removed in vacuo. The resultant brown gum was redissolved in THF (200 mL), cooled to 0° C. and 10% aqueous acetic acid (500 mL) added slowly. Acetonitrile (~200 mL) was added slowly until a brown solid developed; the solid was isolated by filtration and washed with successive portions of diethyl ether and acetonitrile to give the title compound as a yellow crystalline solid (11.0 g, 21%). $\delta_H$ (DMSO-$d_6$) 8.42 (1H, d, J=6.7 Hz), 8.22 (1H, m), 7.73 (1H, m), 7.61 (1H, m), 7.46 (1H, t, J=8.6 Hz), 7.35-7.31 (1H, m). Exchangeable protons were not observed. LCMS (pH 10) RT 1.82 minutes, ES$^+$ 415 (M+H)$^+$, ES$^-$ 413 (M−H)$^-$.

Intermediate 6

N-(2-Fluoro-4-iodophenyl)thieno[2,3-b]pyridin-2-amine

A suspension of Intermediate 5 (3 g, 7.2 mmol) in toluene (50 mL) was heated at reflux for 18 hours. After this time the solvent was removed in vacuo to afford the title compound as a pale brown solid (2.7 g, quant.). $\delta_H$ (CDCl$_3$) 8.42 (1H, dd J 1.6, 4.7 Hz), 7.82 (1H, dd J 1.4, 8.1 Hz), 7.46 (2H, m), 7.27-7.18 (2H, m), 6.77 (1H, s), 6.25 (1H, s). LCMS (pH 10) RT 3.36 minutes, (ES$^+$) 371 (M+H)$^+$.

Intermediate 7

Pentafluorophenyl 2-[(2-fluoro-4-iodophenyl)amino]thieno[2,3-b]pyridine-3-sulfonate A solution of Intermediate 6 (270 mg, 0.73 mmol) in DCM (25 mL) was cooled (acetone/$CO_2$ bath) before chlorosulfonic acid (0.24 ml, 3.65 mmol) was added dropwise. The mixture was placed in an ice bath and stirred for 5 hours, before pyridine (1.2 mL, 14.6 mmol) and then pentafluorophenol (300 mg, 1.6 mmol) were added. After 18 hours the reaction mixture was partitioned between DCM (100 mL) and water (100 mL). The organic layer was dried ($Na_2SO_4$) and concentrated in vacuo and after chromatography ($SiO_2$/DCM) gave the title compound as a white crystalline solid (395 mg. 88%). $\delta_H$ ($CDCl_3$) 8.57 (1H, s), 8.43 (1H, m), 8.15 (1H, m), 7.62 (2H, m), 7.39-7.27 (2H, m). LCMS (pH 3) RT 3.93 minutes, ($ES^+$) 617 $(M+H)^+$.

Intermediate 8 tert-Butyl {[1-({2-[(2-fluoro-4-iodophenyl)amino]thieno[2,3-b]pyridin-3-yl}sulfonyl)-azetidin-3-yl]methyl}carbamate To a solution of Intermediate 7 (190 mg, 0.31 mmol) and pyridine (0.047 mL, 0.60 mmol) in DCM (5 mL) was added azetidin-3-ylmethylcarbamic acid tert-butyl ester (115 mg, 0.62 mmol) and the reaction stirred overnight at ambient temperature. After this time the reaction mixture was diluted with 30 mL of DCM, and washed with 2M HCl (2×25 mL) and water (25 mL). After drying ($Na_2SO_4$) and evaporating in vacuo, the residue was purified by chromatography ($SiO_2$, 30% EtOAc in DCM) to afford the title compound as a white solid (150 mg, 78%). $\delta_H$ ($CDCl_3$) 9.04 (1H, s), 8.39 (1H, dd, J 1.6, 4.7 Hz), 8.20 (1H, dd, J 1.6, 8.1 Hz), 7.58 (2H, m), 7.40 (1H, m), 7.31 (1H, dd, J 4.8, 8.2 Hz), 4.68 (1H, s), 3.95 (2H, dd, J 8.1, 8.1 Hz), 3.63 (2H, m), 3.25 (2H, m), 2.69 (1H, m), 1.41 (9H, s). LCMS (pH 3) RT 3.51 minutes, ($ES^+$) 619 $(M+H)^+$.

Intermediate 9 tert-Butyl 4-({2-[(2-fluoro-4-iodophenyl)amino]thieno[2,3-b]pyridin-3-yl}sulfonyl)piperazine-1-carboxylate Prepared from Intermediate 6 (200 mg, 0.541 mmol) by the method of Example 2 with N—BOC-piperazine (1.0 g, 1.08 mmol) to give after column chromatography ($SiO_2$, 20% EtOAc in DCM) the title compound as an off-white solid (60 mg, 18%). $\delta_H$ ($CDCl_3$) 9.00 (1H, s), 8.40 (1H, dd, J 1.4, 4.8 Hz), 8.16 (1H, dd, J 1.6, 8.2 Hz), 7.58 (2H, m), 7.38 (1H, dd, J 8.6, 8.6 Hz), 7.31 (1H, dd, J 4.7, 8.2 Hz), 3.53 (4H, t, J=4.9 Hz), 3.18 (4H, t, J=4.9 Hz), 1.43 (9H, s). LCMS (pH 10) RT 2.91 minutes, ($ES^+$) 619 $(M+H)^+$.

Intermediate 10

3-Hydroxy-3-(nitromethyl)azetidine-1-carboxylic acid tert-butyl ester

3-Oxoazetidine-1-carboxylic acid tert-butyl ester (500 mg, 2.9 mmol) was dissolved in ethanol (1.5 mL) and to this was added nitromethane (0.6 mL) and triethylamine (cat.). The reaction was stirred for eighteen hours and the solvent was then removed under reduced pressure to yield the title compound as a white solid (650 mg, 97%). $\delta_H$ ($d_6$-DMSO) 6.42 (1H, s), 4.86 (2H, s), 4.04 (2H, d, J 9.2 Hz), 3.75 (2H, d, J 9.2 Hz), 1.39 (9H, s). LCMS ($ES^+$) RT (pH 10) 1.73 min $(M–H)^-$ 231.

Intermediate 11

3-(Aminomethyl)-3-hydroxyazetidine trifluoroacetate salt

Intermediate 10 (500 mg, 2.2 mmol) was dissolved in ethanol (40 mL) in a hydrogenation vessel and 10% palladium on charcoal (43 mg) was added. The vessel was charged with hydrogen to 50 psi and heated to 50° C. This was then stirred for 2 h and the catalyst was removed by filtering through a plug of celite. The solvent was removed under reduced pressure to yield a pale yellow oil. The intermediate was purified by chromatography on an amine column using 5% DCM/MeOH as the eluent to afford the BOC-protected amine as an off-white solid (306 mg, 68%). $\delta_H$ ($d_6$-DMSO) 5.50 (1H, s), 3.73 (2H, d, J 8.5 Hz), 3.54 (2H, d, J 8.5 Hz), 2.60 (2H, s), 1.37 (9H, s). Some exchangeable protons were not observed. The intermediate BOC-protected amine was dissolved in DCM (10 mL) and trifluoroacetic acid (1 mL) added. The mixture was stirred for 1 hour at room temperature before the volatiles were removed in vacuo to give the title compound, which was used without further purification.

Intermediate 12

2-(2-Chloropyridin-3-yl)-N-methoxy-N-methylacetamide

To a suspension of (2-chloropyridin-3-yl)acetic acid (Intermediate 3; 2.0 g, 11.6 mmol) in DCM (100 mL) was added N,O-dimethylhydroxylamine hydrochloride (1.19 g, 12.2 mmol), N-methylmorpholine (3.8 mL, 34.8 mmol) and EDC (2.3 g, 12.2 mmol). The mixture was stirred at room temperature for 48 hours, diluted with DCM (100 mL), washed with 10% HCl (aq) solution (200 mL) and brine (200 mL), dried ($Na_2SO_4$), filtered and the solvents removed in vacuo. The crude product was purified by column chromatography ($SiO_2$, 1:1 EtOAc:DCM) to give the title compound as a white waxy solid (2.2 g, 88%). $\delta_H$ (DMSO-$d_6$) 8.31 (1H, dd, J 4.7, 1.9 Hz), 7.81 (1H, dd, J 7.5, 1.9 Hz), 7.40 (1H, dd, J 7.5, 4.7 Hz), 3.93 (2H, s), 3.76 (3H, s), 3.15 (3H, s). LCMS (pH 3) RT 2.22 minutes, ($ES^+$) 215 $^{35}Cl$ $(M+H)^+$, 217 $^{37}Cl$ $(M+H)^+$.

Intermediate 13

1-(2-Chloropyridin-3-yl)propan-2-one

To a solution of Intermediate 12 (200 mg, 0.93 mmol) in anhydrous THF (10 mL) under nitrogen was added dropwise a solution of methylmagnesium bromide (0.33 mL, 3M in diethyl ether, 0.97 mmol). The reaction mixture was allowed to stir at ambient temperature for 30 minutes before 10% aqueous HCl (2 mL) was added followed by 2M NaOH (50 mL). The mixture was extracted with EtOAc (3×50 mL), the combined organic phases washed with brine, dried ($Na_2SO_4$), filtered and the solvents removed in vacuo to give the title compound as a pale yellow solid (154 mg, 97%). $\delta_H$ ($CDCl_3$) 8.35 (1H, dd, J 4.8, 1.9 Hz), 7.58 (1H, dd, J 6.5, 1.9 Hz), 7.25 (1H, dd, J 6.5, 4.8 Hz), 3.89 (2H, s), 2.30 (3H, s). LCMS (pH 3) RT 2.03 minutes, ($ES^+$) 170 $^{35}Cl$ $(M+H)^+$, 172 $^{37}Cl$ $(M+H)^+$.

Intermediate 14

2-[(2-Fluoro-4-iodophenyl)amino]thieno[2,3-b]pyridine-3-carbonitrile

To a solution of (2-chloropyridin-3-yl)acetonitrile (Intermediate 2; 700 mg, 4.59 mmol) and Intermediate 4 (1.28 g, 4.60 mmol) in dry DMSO (15 mL) was added sodium hydride (202 mg, 60% in mineral oil, 5.06 mmol). The mixture was stirred at room temperature for 15 minutes before heating to 90° C. for four hours. The reaction mixture was poured into water (80 mL) and the solid precipitate filtered and washed with water/ethanol (2:1 mixture, 50 mL) followed by diethyl ether/hexane (1:1 mixture, 20 mL). The solid was dried in a vacuum oven and recrystallised from ethanol/water to give the title compound as a pale brown solid (800 mg, 45%). $\delta_H$ (DMSO-$d_6$) 10.40 (1H, s), 8.37 (1H, dd, J 1.3, 4.6 Hz), 7.83-7.81 (2H, m), 7.64 (1H, d, J 8.3 Hz), 7.44 (1H, dd, J 4.7, 8.0 Hz), 7.33 (1H, dd, J 8.3, 8.3 Hz). LCMS RT 3.08 minutes, (ES$^-$) 394 (M–H)$^-$, (ES$^+$) 396 (M+H)$^+$.

Intermediate 15

N'-Acetyl-2-[(2-fluoro-4-iodophenyl)amino]thieno[2,3-b]pyridine-3-carbohydrazide To a solution of Intermediate 5 (200 mg, 0.48 mmol) in DMF (20 mL) was added PyBrOP (444 mg, 0.97 mmol), N-acetylhydrazide (69 mg, 0.97 mmol) and N,N-di-isopropylethylamine (0.74 mL, 0.96 mmol). The resulting mixture was stirred overnight at ambient temperature. After this time the reaction mixture was diluted with water (50 mL) and the resulting precipitate was filtered to give the title compound as an off-white solid (187 mg, 41%) which was used in the next step without further purification. LCMS (pH 10) RT 2.17 minutes, (ES$^+$) 471.1 (M+H)$^+$.

Intermediate 16

2-[(2-Fluoro-4-iodophenyl)amino]-N'-(phenylcarbonyl)thieno[2,3-b]pyridine-3-carbohydrazide Intermediate 5 (250 mg, 0.60 mmol) in DMF (20 mL) was treated with PyBrOP (559 mg, 1.2 mmol), benzoic hydrazide (164 mg, 1.2 mmol) and N,N-diisopropylethylamine (1.0 mL, 1.2 mmol) and stirred overnight at room temperature. After this time the reaction mixture was diluted with water (50 mL). The resulting brown-coloured precipitate (125 mg, 40%) was filtered off and taken on to the next step without further purification. LCMS (pH 10) RT 2.65 minutes, (ES$^+$) 533 (M+H)$^+$.

Intermediate 17

(Morpholin-4-yl)-(pyridin-4-yl)-acetonitrile p-Toluenesulphonic acid (1.91 g, 10.1 mmol) in THF (10 mL) was treated portionwise with morpholine (1.75 g, 1.76 mL, 20.1 mmol) and 4-pyridinecarbox-aldehyde (1 g, 9.3 mmol) was added with stirring. The reaction mixture was heated at 100° C. for 2 h. After cooling to room temperature potassium cyanide (0.82 g, 12.6 mmol) was added as a slurry in water (1.5 mL) and the reaction mixture heated for 18 h at reflux. After cooling to room temperature the THF was removed in vacuo and the residue extracted with DCM, dried over sodium sulphate, concentrated, dissolved in ethyl acetate, then filtered through a pad of silica eluting with ethyl acetate. The residue was chromatographed on silica in DCM/ethyl acetate (0-100% gradient) to give the title compound (1.5 g). $\delta_H$ (DMSO-$d_6$) 8.68-8.64 (2H, m), 7.49-7.46 (2H, m), 5.53 (1H, s), 3.66-3.60 (4H, m), 2.59-2.51 (2H, m), 2.43-2.35 (2H, m).

Intermediate 18

3-(2-Chloropyridin-3-yl)-2-(morpholin-4-yl)-3-(pyridin-4-yl)propionitrile

Intermediate 17 (0.5 g, 2.46 mmol) in THF (10 mL) under nitrogen was cooled to 0° C. and treated with Intermediate 1 (400 mg, 2.46 mmol) and sodium hydride (98 mg, 2.46 mmol). After stirring at 0° C. for 2 h the reaction mixture was allowed to warm to room temperature and stirred for 18 h. The reaction mixture was quenched with water and extracted into DCM, dried (sodium sulphate) and concentrated. The residue was chromatographed on silica in DCM/ethyl acetate (gradient elution 0-100%) to give the title compound (550 mg). $\delta_H$ (DMSO-$d_6$) 8.56-8.52 (2H, m), 8.25 (1H, dd, J 4.5, 1.9 Hz), 7.49-7.46 (1H, m), 7.41 (1H, dd, J 7.7, 1.9 Hz), 7.27-7.22 (2H, m), 3.90 (1H, d, J 13.8 Hz), 3.82-3.60 (4H, m), 3.32 (1H, d, J 13.8 Hz), 2.85-2.75 (2H, m), 2.42-2.33 (2H, m). LCMS (pH 3) RT 1.65 minutes, (ES$^+$) 329/331 (M+H)$^+$.

Intermediate 19

2-(2-Chloropyridin-3-yl)-1-(pyridin-4-yl)ethanone

Intermediate 18 (0.5 g, 2.54 mmol) was treated with 2M HCl (5 mL) and stirred at 50° C. for 4 h. After treatment with 2M NaOH (until pH=10) the product was extracted into DCM, dried (sodium sulphate), filtered and concentrated in vacuo. Chromatography on silica in DCM/diethyl ether (0 to 100% gradient) yielded the title compound (260 mg). $\delta_H$ (DMSO-$d_6$) 8.88 (2H, m), 8.37 (1H, dd, J 4.7, 1.9 Hz), 7.95 (2H, m), 7.88 (1H, dd, J 7.5, 1.9 Hz), 7.46 (1H, m), 4.67 (2H, s). LCMS (pH 3) RT 1.39 minutes, (ES$^+$) 233/235 (M+H)$^+$.

Intermediate 20

3-Bromo-2-(methylsulphanyl)thieno[2,3-b]pyridine n-Butyllithium (3.25 mL, 1.7M in hexanes, 5.2 mmol) was added to a cooled solution of diisopropylamine (0.74 mL, 5.2 mmol) in THF (15 mL) at −78° C. The reaction mixture was allowed to warm to room temperature and stirred for 30 minutes. The reaction was cooled to 0° C. and 3-bromothieno[2,3-b]pyridine (prepared by the method of Klemm L. H. et al., *Journal of Heterocyclic Chemistry*, 1974, 11(2), 205-209) (1 g, 4.7 mmol) added. After stirring for a further 20 minutes dimethyl disulphide (443 mg, 0.42 mL, 4.7 mmol) was added, and the reaction mixture was allowed to warm to room temperature and stirred for 1 h. The reaction was quenched with water, extracted into DCM, dried (sodium sulphate), filtered and concentrated in vacuo. Chromatography (silica; DCM) yielded the title compound as a pale yellow solid (850 mg). $\delta_H$ (DMSO-$d_6$) 8.57 (1H, dd, J 4.7, 1.5 Hz), 8.00 (1H, m), 7.54 (1H, dd, J 8.1, 4.5 Hz), 2.70 (3H, m). LCMS (pH 3) RT 2.64 minutes, (ES$^+$) 259/261 (M+H)$^+$.

Intermediate 21

2-{(Hydroxy)-[2-(methylsulphanyl)thieno[2,3-b]pyridin-3-yl]-methyl]pyrrolidine-1-carboxylic acid tert-butyl ester Intermediate 20 (250 mg, 0.97 mmol) in THF (10 mL) at −100° C. was treated with n-butyllithium (0.42 mL, 1.7M in hexanes, 1.05 mmol) and stirred for 30 minutes. 2-Formylpyrrolidine-1-carboxylic acid tert-butyl ester (193 mg, 0.97 mmol) was added and the reaction stirred for a further 15 minutes at −100° C. then allowed to warm to room temperature. The reaction was quenched with water, extracted into DCM, dried (sodium sulphate), filtered, concentrated in vacuo and chromatographed on silica in DCM/ethyl acetate (0-100% gradient) to give the title compound (330 mg). LCMS (pH 3) RT 2.50 minutes (48%, diastereoisomer A), 2.83 minutes (44%, diastereoisomer B), (ES$^+$) 381 (M+H)$^+$.

Intermediate 22

2-[2-(Methylsulphanyl)thieno[2,3-b]pyridine-3-carbonyl]pyrrolidine-1-carboxylic acid tert-butyl ester Intermediate 21 (350 mg, 0.92 mmol) in DCM (10 mL) was treated with Dess-Martin periodinane (390 mg, 0.92 mmol) and stirred at room temperature for 3 h. The reaction was quenched with water, extracted into DCM, dried (sodium sulphate), filtered, concentrated in vacuo and chromatographed on silica in DCM/ethyl acetate (0-100%) to give the title compound (200 mg). $\delta_H$ (DMSO-d$_6$) 8.54-8.50 (1.4H, m), 8.43 (0.6H, dd, J 8.5, 1.3 Hz), 7.57-7.51 (1H, m), 5.25-5.18 (1H, m), 3.58-3.48 (1H, m), 3.43-3.33 (1H, m), 2.74 (1.8H, s), 2.72 (1.2H, s), 1.97-1.78 (4H, m), 1.41 (3.6H, m), 1.16 (5.4H, m). Two diastereoisomers; ratio 0.4:0.6. LCMS (pH 3) RT 2.74 minutes, (ES$^+$) 379 (M+H)$^+$.

Intermediate 23

2-[2-(Methanesulphinyl)thieno[2,3-b]pyridine-3-carbonyl]pyrrolidine-1-carboxylic acid tert-butyl ester Intermediate 22 (200 mg, 0.53 mmol) in methanol (3 mL) and water (1 mL) at 0° C. was treated with Oxone® (325 mg, 0.53 mmol) and stirred at 0° C. for 1 h then allowed to warm to room temperature for 2 h. The reaction was diluted with water, extracted into DCM, dried (sodium sulphate), filtered, concentrated in vacuo and chromatographed on silica in DCM/ethyl acetate (0-100%) to give the title compound (200 mg). LC (pH 3) RT 1.75 minutes (38%), 1.88 minutes (62%); mixture of diastereoisomers.

Intermediate 24

2-[2-(2-Fluoro-4-iodophenylamino)thieno[2,3-b]pyridine-3-carbonyl]pyrrolidine-1-carboxylic acid tert-butyl ester 2-Fluoro-4-iodoaniline (360 mg, 1.53 mmol) in THF (10 mL) was treated with 1M lithium hexamethyldisilazide (1.68 mL, 1.68 mmol) at 0° C. and stirred for 10 minutes. Intermediate 23 (200 mg, 0.51 mmol) in THF (5 mL) was added and the reaction allowed to warm to room temperature and stirred for 2 h. The reaction was quenched with water, extracted into DCM, dried (sodium sulphate), filtered, concentrated in vacuo and chromatographed (silica; diisopropyl ether) to give the title compound (180 mg). $\delta_H$ (DMSO-d$_6$) 8.37 (1H, d, J 4.3 Hz), 8.27-8.16 (1H, m), 7.91-7.84 (1H, m), 7.75-7.42 (4H, m), 5.20-5.08 (1H, m), 3.64-3.49 (1H, m), 3.48-3.34 (1H, m), 2.03-1.83 (4H, m), 1.42 (3H, s), 1.36 (6H, s). Two rotamers; ratio 2:1. LCMS (pH 3) RT 2.589 minutes, (ES$^+$) 568 (M+H)$^+$.

Intermediate 25

4-{(Hydroxy)-[2-(methylsulphanyl)thieno[2,3-b]pyridin-3-yl]-methyl}piperidine-1-carboxylic acid benzyl ester Intermediate 20 (350 mg, 1.35 mmol) in THF (10 mL) was cooled to −100° C., treated with n-butyllithium (0.57 mL, 2.5M in hexanes, 1.41 mmol) and stirred for 30 minutes. 1-(Benzyloxycarbonyl)pyrrolidine-4-carboxaldehyde (333 mg, 1.35 mmol) was added and the reaction stirred for 15 minutes before being allowed to warm to room temperature. After quenching with water the product was extracted into DCM, dried (sodium sulphate), filtered, concentrated in vacuo and chromatographed on silica in DCM/ethyl acetate (0-100%) to give the title compound (435 mg). LCMS (pH 3) RT 2.75 minutes, (ES$^+$) 429 (M+H)$^+$.

Intermediate 26

4-[2-(Methylsulphanyl)thieno[2,3-b]pyridine-3-carbonyl]piperidine-1-carboxylic acid benzyl ester Intermediate 25 (420 mg, 0.98 mmol) in DCM (5 mL) was treated with Dess-Martin periodinane (416 mg, 0.98 mmol) and stirred at room temperature for 3 h. The reaction mixture was partitioned between DCM and water, then the organic phase was washed with sodium hydrogencarbonate solution, dried (sodium sulphate), filtered, concentrated in vacuo and chromatographed on silica in DCM/ethyl acetate (1:1) to give the title compound (420 mg). LCMS (pH 3) RT 3.06 minutes, (ES$^+$) 427 (M+H)$^+$.

Intermediate 27

4-[2-(Methanesulphinyl)thieno[2,3-b]pyridine-3-carbonyl]piperidine-1-carboxylic acid benzyl ester Intermediate 26 (0.42 g, 0.98 mmol) in methanol (9 mL) and water (3 mL) was treated with Oxone® (427 mg, 0.98 mmol) and stirred at room temperature for 2 h. The reaction was diluted with water, extracted into DCM, dried (sodium sulphate), filtered, concentrated in vacuo and chromatographed on silica in DCM/ethyl acetate (0-100%) to give the title compound (290 mg). $\delta_H$ (DMSO-d$_6$) 8.81-8.77 (1H, m), 8.71 (1H, dd, J 8.5, 1.3 Hz), 7.75 (1H, dd, J 8.3, 4.5 Hz), 7.47-7.37 (5H, m), 5.14 (2H, s), 4.15-3.98 (2H, m), 3.75-3.65 (1H, m), 3.26-3.12 (2H, m), 3.09 (3H, s), 2.05-1.97 (1H, m), 1.95-1.84 (1H, m), 1.68-1.42 (2H, m). LCMS RT 2.21 minutes, (ES$^+$) 443 (M+H)$^+$.

Intermediate 28

4-[2-(2-Fluoro-4-iodophenylamino)thieno[2,3-b]pyridine-3-carbonyl]piperidine-1-carboxylic acid benzyl ester 2-Fluoro-4-iodoaniline (467 mg, 1.97 mmol) in THF (10 mL) was cooled to 0° C. and treated with 1M lithium hexamethyldisilazide solution in THF (2.17 mL, 2.17 mmol) and stirred at 0° C. for 10 minutes. Intermediate 27 (290 mg, 0.66 mmol) in THF (2 mL) was added, and the reaction stirred at room temperature for 30 minutes. The reaction was quenched with water, extracted into DCM, dried (sodium sulphate), filtered, concentrated in vacuo and chromatographed on silica in tert-butylmethyl ether/DCM (0-100%) to give the title compound (300 mg). $\delta_H$ (DMSO-d$_6$) 8.37-8.32 (1H, m), 8.19-

8.13 (1H, m), 7.88-7.82 (1H, m), 7.74-7.61 (2H, m), 7.54 (1H, t, J 8.7 Hz), 7.47 (1H, dd, J 8.3, 4.9 Hz), 7.38-7.29 (5H, m), 5.08 (2H, s), 4.15-4.02 (2H, m), 3.54-3.42 (1H, m), 3.19-3.08 (2H, m), 1.92-1.82 (2H, m), 1.65-1.51 (2H, m). LCMS (pH 3) RT 3.96 minutes, (ES$^+$) 616 (M+H)$^+$.

Intermediate 29

3-{(Hydroxy)-[2-(methylsulphanyl)thieno[2,3-b]pyridin-3-yl]-methyl}azetidine-1-carboxylic acid tert-butyl ester Intermediate 20 (650 mg, 2.5 mmol) in THF (20 mL) was cooled to −100° C. and treated with n-butyllithium and allowed to stir for 30 minutes at −100° C. 1-(tert-Butoxycarbonyl)azetidine-3-carboxaldehyde (0.46 g, 2.5 mmol) in THF (2 mL) was added and the reaction allowed to warm to room temperature. After quenching with water the product was extracted into DCM, dried (sodium sulphate), filtered and concentrated in vacuo. Chromatography on silica in DCM/ethyl acetate (0-100%) gave the title compound (570 mg). $\delta_H$ (DMSO-d$_6$) 8.49 (1H, m), 8.38 (1H, dd, J 8.1, 1.5 Hz), 7.42-7.37 (1H, m), 5.93 (1H, d, J 4.0 Hz), 5.22 (1H, dd, J 9.2, 4.0 Hz), 3.99-3.84 (2H, m), 3.71-3.63 (1H, m), 3.49 (1H, dd, J 8.3, 5.5 Hz), 3.11-2.99 (1H, m), 2.63 (3H, s), 1.37 (9H, s). LCMS (pH 3) RT 2.44 minutes, (ES$^+$) 367 (M+H)$^+$.

Intermediate 30

3-[2-(Methylsulphanyl)thieno[2,3-b]pyridine-3-carbonyl)azetidine-1-carboxylic acid tert-butyl ester Intermediate 29 (570 mg, 1.56 mmol) in DCM (10 mL) was treated with Dess-Martin periodinane (660 mg, 1.56 mmol) and stirred at room temperature for 3 h. The reaction was quenched with water, extracted into DCM, washed with sodium hydrogen-carbonate solution, dried over sodium sulphate, filtered and concentrated in vacuo. The title compound (550 mg) was used without further purification. $\delta_H$ (DMSO-d$_6$) 8.51 (1H, dd, J 4.5, 1.3 Hz), 8.33 (1H, dd, J 8.5, 1.5 Hz), 7.52 (1H, dd, J 8.5, 4.7 Hz), 4.36-4.26 (1H, m), 4.25-4.15 (2H, m), 4.03-3.95 (2H, m), 2.72 (3H, s), 1.39 (9H, s). LCMS (pH 3) RT 2.72 minutes, (ES$^+$) 365 (M+H)$^+$.

Intermediate 31

3-[2-(Methanesulphinyl)thieno[2,3-b]pyridine-3-carbonyl]azetidine-1-carboxylic acid tert-butyl ester Intermediate 30 (550 mg, 1.5 mmol) in methanol (1 mL) and water (3 mL) was treated with Oxone® (600 mg, 1.5 mmol) and stirred at room temperature for 2 h. The reaction was diluted with water, extracted into DCM, dried (sodium sulphate), filtered and concentrated in vacuo. Chromatography on silica in DCM/ethyl acetate (0-100%) gave the title compound (250 mg). $\delta_H$ (CDCl$_3$) 8.69 (1H, dd, J 4.5, 1.5 Hz), 8.15 (1H, dd, J 8.5, 1.5 Hz), 7.51 (1H, dd, J 8.5, 4.5 Hz), 4.36-4.13 (5H, m), 3.11 (3H, s), 1.44 (9H, s). LCMS (pH 3) RT 2.01 minutes, (ES$^+$) 381 (M+H$^+$).

Intermediate 32

3-[2-(2-Fluoro-4-iodophenylamino)thieno[2,3-b]pyridine-3-carbonyl]azetidine-1-carboxylic acid tert-butyl ester 2-Fluoro-4-iodoaniline (310 mg, 1.31 mmol) in THF (5 mL) was treated with 1M lithium hexamethyldisilazide in THF (1.44 mL, 1.44 mmol) and stirred at 0° C. for 10 minutes. Intermediate 31 (250 mg, 0.66 mmol) in THF (2 mL) was added and the reaction stirred for 30 minutes. After quenching with water the product was extracted into DCM, dried (sodium sulphate), filtered, concentrated in vacuo and chromatographed on silica in DCM/tert-butylmethyl ether (0-100%) to give the title compound (80 mg). $\delta_H$ (DMSO-d$_6$) 11.94 (1H, s), 8.30-8.25 (1H, m), 8.15-7.96 (1H, m), 7.81 (1H, dd, J 10.2, 1.5 Hz), 7.66-7.60 (1H, m), 7.48 (1H, t, J 8.5 Hz), 7.39-7.33 (1H, m), 4.25-3.99 (3H, m), 4.02-3.94 (2H, m), 1.29 (9H, s). LCMS (pH 3) RT 3.74 minutes, (ES$^+$) 554 (M+H)$^+$.

Example 1

N-(2-Fluoro-4-iodophenyl)-3-(pyrrolidin-1-ylsulfonyl)thieno[2,3-b]pyridin-2-amine To a solution of Intermediate 6 (60 mg, 0.16 mmol) in DCM (5 mL), cooled in a CO$_2$/acetone bath, was added chlorosulfonic acid (200 mg, 1.72 mmol) dropwise. The reaction mixture was placed in an ice bath and stirred for a further 5 hours. After this time pyrrolidine (250 mg, 3.5 mmol) was slowly added and the reaction stirred for 18 hours at ambient temperature. The reaction mixture was diluted with DCM (25 mL) and washed with water (20 mL), 2M HCl (20 mL) and water (20 mL). The organic phases were dried (Na$_2$SO$_4$) and evaporated in vacuo. The product was recrystallised from acetonitrile/water to afford the title compound (30 mg, 37%) as an off-white solid. $\delta_H$ (CDCl$_3$) 9.12 (1H, s), 8.38 (1H, dd, J 4.8, 1.5 Hz), 8.24 (1H, dd, J 8.1, 1.5 Hz), 7.57 (2H, m), 7.40 (2H, m), 3.38 (4H, t, J 6.6 Hz), 1.89 (4H, t, J 6.6 Hz). LCMS (pH 3) RT 3.95 minutes, (ES$^+$) 504 (M+H)$^+$.

Example 2

3-{[3-(Aminomethyl)azetidin-1-yl]sulfonyl}-N-(2-fluoro-4-iodophenyl)thieno[2,3-b]pyridin-2-amine Intermediate 8 (140 mg, 0.23 mmol) was treated with a 20% solution of TFA in DCM (5 mL). The reaction mixture was stirred for three hours at room temperature, before diluting with 25 mL of DCM and washing with NaHCO$_3$ solution (25 mL) and then water (25 mL). The organic layer was dried (Na$_2$SO$_4$) and evaporated in vacuo to give the title compound as a white powder (89 mg, 75%). $\delta_H$ (DMSO-d$_6$) 8.26 (1H, s), 8.08 (1H, dd, J 1.6, 4.7 Hz), 7.92 (1H, dd, J 1.6, 8.1 Hz), 7.66 (1H, dd, J 1.9, 10.1 Hz), 7.53 (1H, dd, J 2.0, 8.3 Hz), 7.23 (2H, m), 3.92 (2H, t, J 8.2 Hz), 3.65 (2H, m), 2.80 (2H, d, J 7.3 Hz), 2.54 (1H, m). Exchangeable protons were not observed. LCMS (pH 10) RT 2.73 minutes, (ES$^+$) 519 (M+H)$^+$.

Example 3 tert-Butyl[(3R)-1-({2-[(2-fluoro-4-iodophenyl)amino]thieno[2,3-b]pyridin-3-yl}sulfonyl)pyrrolidin-3-yl]carbamate To a solution of Intermediate 7 (300 mg, 0.48 mmol) and pyridine (0.075 mL, 0.96 mmol) in DCM (5 mL) was added pyrrolidinyl-3(R)-carbamic acid tert-butyl ester (76 mg, 0.96 mmol) and the reaction was stirred overnight at ambient temperature. After this time the reaction mixture was diluted with DCM (35 mL), and washed with 2M HCl (2×25 mL) and water (25 mL). The organic phases were dried (Na$_2$SO$_4$), filtered and the solvents removed in vacuo to give a crude residue. Purification by column chromatography (SiO$_2$, 25% EtOAc in DCM) gave the title compound as a white solid (300 mg, 100%). δ$_H$ (CDCl$_3$) 8.98 (1H, s), 8.30 (1H, dd, J 1.2, 4.6 Hz), 8.10 (1H, dd, J 1.2, 8.1 Hz), 7.50 (2H, m), 7.30 (1H, m), 7.27 (1H, dd, J 4.7, 8.2 Hz), 4.55 (1H, br s), 4.11 (1H, s), 3.45 (2H, m), 3.20 (2H, m), 2.10 (1H, m), 1.70 (1H, m), 1.33 (9H, s). LCMS (pH 3) RT 3.54 minutes, (ES$^+$) 619 (M+H)$^+$.

Example 4

3-{[(3R)-3-Aminopyrrolidin-1-yl]sulfonyl}-N-(2-fluoro-4-iodophenyl)thieno[2,3-b]pyridin-2-amine Example 3 (300 mg, 0.48 mmol) was treated with a 20% solution of TFA in DCM (5 mL). The reaction mixture was stirred for three hours at room temperature before being diluted with DCM (25 mL) and washed with NaHCO$_3$ solution (25 mL) and water (25 mL). The organic layer was dried (Na$_2$SO$_4$) and evaporated in vacuo to give the title compound as an off-white powder (230 mg, 92%). δ$_H$ (DMSO-d$_6$) 8.15 (1H, dd, J 1.5, 4.7 Hz), 8.04 (1H, dd, J 1.5, 8.1 Hz), 7.70 (1H, dd, J 1.8, 10.1 Hz), 7.57 (1H, d, J 8.4 Hz), 7.33-7.24 (2H, m), 5.26 (2H, br s), 3.47 (2H, t, J 6.5 Hz), 3.35 (2H, m), 2.99 (1H, m), 1.98 (1H, m), 1.59 (1H, m). One exchangeable proton was not observed. LCMS (pH 3) RT 1.92 minutes, (ES$^+$) 519 (M+H)$^+$.

Example 5 tert-Butyl [(3S)-1-({2-[(2-fluoro-4-iodophenyl)amino]thieno[2,3-b]pyridin-3-yl}sulfonyl)pyrrolidin-3-yl]carbamate To a solution of Intermediate 7 (150 mg, 0.24 mmol) and pyridine (0.038 mL, 0.48 mmol) in DCM (5 mL) was added pyrrolidinyl-3(S)-carbamic acid tert-butyl ester (38 mg, 0.48 mmol) and the reaction mixture stirred overnight at room temperature. After this time the reaction mixture was diluted with DCM (35 mL) and washed with 2M HCl (2×25 mL) and water (25 mL). After drying (Na$_2$SO$_4$) and evaporation in vacuo, the residue was purified by chromatography (SiO$_2$, 25% EtOAc in DCM) to afford the title compound as an off-white solid (132 mg, 89%). δ$_H$ (CDCl$_3$) 8.98 (1H, s), 8.30 (1H, dd, J 1.6, 4.6 Hz), 8.10 (1H, dd, J 1.6, 8.1 Hz), 7.50 (2H, m), 7.30 (1H, m), 7.27 (1H, dd, J 4.7, 8.2 Hz), 4.55 (1H, br s), 4.11 (1H, s), 3.45 (2H, m), 3.20 (2H, m), 2.10 (1H, m), 1.70 (1H, m), 1.33 (9H, s). LCMS (pH 3) RT 3.56 minutes, (ES$^+$) 619 (M+H)$^+$.

Example 6

3-{[(3S)-3-Aminopyrrolidin-1-yl]sulfonyl}-N-(2-fluoro-4-iodophenyl)thieno[2,3-b]pyridin-2-amine Example 5 (132 mg, 0.21 mmol) was treated with a 20% solution of TFA in DCM (5 mL). The reaction mixture was stirred for three hours at room temperature before being diluted with DCM (25 mL) and washed with saturated aqueous NaHCO$_3$ solution (25 mL) and water (25 mL). The organic layer was dried (Na$_2$SO$_4$) and evaporated in vacuo to give the title compound as an off-white powder (66 mg, 61%). δ$_H$ (DMSO-d$_6$) 8.15 (1H, dd, J 1.5, 4.7 Hz), 8.04 (1H, dd, J 1.5, 8.1 Hz), 7.70 (1H, dd, J 1.8, 10.1 Hz), 7.57 (1H, d, J 8.4 Hz), 7.33-7.24 (2H, m), 5.26 (2H, br s), 3.47 (2H, t, J 6.5 Hz), 3.35 (2H, m), 2.99 (1H, m), 1.98 (1H, m), 1.59 (1H, m). One exchangeable proton was not observed. LCMS (pH 3) RT 1.92 minutes, (ES$^+$) 519 (M+H)$^+$.

Example 7

N-(2-Fluoro-4-iodophenyl)-3-(piperazin-1-ylsulfonyl)thieno[2,3-b]pyridin-2-amine hydrochloride To a solution of Intermediate 9 (60 mg, 0.096 mmol) in 1,4-dioxane (5 mL) was added 4M HCl in 1,4-dioxane (10 mL) and the solution stirred at ambient temperature for 3 hours. The volatiles were then removed in vacuo to give the title compound as an off-white solid (50 mg, quant.). δ$_H$ (DMSO-d$_6$) 9.13 (1H, s), 9.02 (1H, s), 8.37 (1H, dd, J 1.5, 4.7 Hz), 8.11 (1H, dd, J 1.5, 8.2 Hz), 7.87 (1H, dd, J 1.8, 9.8 Hz), 7.70 (1H, dd, J 1.0, 8.3 Hz), 7.43 (2H, m), 3.40 (4H, m), 3.19 (4H, m). LCMS (pH 10) RT 3.60 minutes, (ES$^+$) 519 (M+H)$^+$.

Example 8

N,N-Diisopropyl-2-[(2-fluoro-4-iodophenyl)amino]thieno[2,3-b]pyridine-3-sulfonamide Prepared from Intermediate 6 (100 mg, 0.267 mmol) by the method of Example 1 with diisopropylamine (2 mL, 13.7 mmol) to give after column chromatography (SiO$_2$, 25% EtOAc in hexanes) the title compound as an off-white solid (59 mg, 41%). δ$_H$ (DMSO-d$_6$) 9.26 (1H, s), 8.40 (1H, m), 8.17 (1H, m), 7.89 (1H, m), 7.75 (1H, m), 7.53 (2H, m), 3.85 (2H, q, J 6.8 Hz), 2.28 (12H, d, J 6.8 Hz). LCMS (pH 3) RT 3.89 minutes, (ES$^+$) 534 (M+H)$^+$.

Example 9

2-[(2-Fluoro-4-iodophenyl)amino]-N-(2-hydroxyethyl)thieno[2,3-b]pyridine-3-sulfonamide Prepared from Intermediate 7 (150 mg, 0.24 mmol) by the method of Example 3 with 2-aminoethanol (30 μL, 0.49 mmol) to give the title compound as an off-white solid (70 mg, 60%). δ$_H$ (DMSO-d$_6$) 9.10 (1H, s), 8.35 (1H, s), 8.17 (1H, d, J 7.6 Hz), 7.95 (1H, s), 7.83 (1H, d, J=9.7 Hz), 7.66 (1H, d, J 8.3 Hz), 7.46 (2H, m), 4.69 (1H, t, J 5.3 Hz), 3.38 (2H, m), 2.98 (2H, m). One exchangeable proton was not observed. LCMS (pH 3) RT 2.62 minutes, (ES$^+$) 494 (M+H)$^+$.

Example 10

3-(Aminomethyl)-1-({2-[(2-fluoro-4-iodophenyl)amino]thieno[2,3-b]pyridin-3-yl}sulfonyl)azetidin-3-ol Prepared from Intermediate 7 (170 mg, 0.28 mmol) by the method of Example 3 with Intermediate 11 (100 mg, 0.94 mmol) to give after prep LC the title compound as a white solid (9 mg, 2%). δ$_H$ (DMSO-d$_6$) 8.24 (1H, s), 8.11 (1H, d, J 4.4 Hz), 7.95 (1H, m), 7.70 (1H, m), 7.57 (1H, m), 7.29-7.22 (2H, m), 5.85 (1H, s), 3.79 (2H, d, J 8.3 Hz), 3.61 (2H, d, J 8.3 Hz), 2.74 (2H, s). Some exchangeable protons were not observed. LCMS (pH 3) RT 2.00 minutes, (ES$^+$) 535 (M+H)$^+$.

Example 11

Ethyl N-{[1-({2-[(2-fluoro-4-iodophenyl)amino]thieno[2,3-b]pyridin-3-yl}sulfonyl)azetidin-3-yl]methyl}-beta-alaninate To a stirring mixture of Example 2 (160 mg, 0.31 mmol) and N,N-diisopropyl-ethylamine (57 μL, 31 mmol) in DMF (5 mL) was added ethyl acrylate (51 μL, 0.31 mmol) and the mixture allowed to stir for 18 hours. After this time EtOAc (25 mL) was added to the reaction mixture which was then washed with brine (3×25 mL), dried (sodium sulfate) and then reduced in vacuo. The resulting oil was purified by column chromatography (SiO$_2$, 50% DCM in EtOAc) to afford the title compound as a colourless oil (71 mg, 38%). $\delta_H$ (CDCl$_3$) 8.97 (1H, s), 8.30 (1H, dd, J 1.6, 4.7 Hz), 8.12 (1H, dd, J 1.6, 8.2 Hz), 7.51 (2H, m), 7.33 (1H, dd, J 8.7, 8.7 Hz), 7.23 (1H, dd, J 4.7, 8.2 Hz), 4.04 (2H, q, J 7.2 Hz), 3.88 (2H, dd, J 8.0, 8.0 Hz), 3.55 (2H, dd, J 5.6, 8.0 Hz), 2.71 (2H, t, J 6.3 Hz), 2.64 (2H, d, J 7.3 Hz), 2.53 (1H, m), 2.33 (2H, t, J 6.3 Hz), 1.17 (3H, t, J 7.2 Hz). Exchangeable protons were not observed. LCMS (pH 10) RT 3.19 minutes, (ES$^+$) 619 (M+H).

Example 12

Ethyl N-{[1-({2-[(2-fluoro-4-iodophenyl)amino] thieno[2,3-b]pyridin-3-yl}sulfonyl)azetidin-3-yl] methyl}glycinate To a stirring mixture of Example 2 (200 mg, 0.39 mmol) and N,N-diisopropyl-ethylamine (68 µL, 42 mmol) in DMF (5 mL) was added ethyl bromoacetate (43 µL, 0.39 mmol) and the mixture allowed to stir for 18 hours. After this time EtOAc (25 mL) was added to the reaction mixture which was then washed with brine (3×25 mL), dried (sodium sulfate) and then reduced in vacuo. The resulting oil was purified by column chromatography (SiO$_2$, 50% DCM in EtOAc) to afford the title compound as a white solid (47 mg, 20%). LCMS (pH 3) RT 2.24 minutes, (ES$^+$) 605 (M+H).

Example 13

1-({2-[(2-Fluoro-4-iodophenyl)amino]thieno[2,3-b] pyridin-3-yl}sulfonyl)azetidin-3-ol Intermediate 3 (150 mg, 0.25 mmol) was dissolved in dichloromethane (6 mL) and triethylamine (75 µL, 0.50 mmol) and 3-hydroxyazetidine HCl salt (55 mg, 0.50 mmol) were added. The reaction mixture was stirred at ambient temperature under nitrogen for 18 hours. Dichloromethane (20 mL) was added and the solution washed with water (10 mL), dried (Na$_2$SO$_4$) and concentrated in vacuo. The residue was triturated with diethyl ether (10 mL) to remove pentafluorophenol. The crude product was purified by prep HPLC to give after freeze-drying the title compound as a white solid (50 mg, 39%). $\delta_H$ (DMSO-d$_6$) 8.27 (1H, s), 8.21 (1H, d, J 3.5 Hz), 8.00 (1H, dd, J 1.4, 8.3 Hz), 7.76 (1H, dd, J 1.8, 10.0 Hz), 7.61 (1H, d, J 8.3 Hz), 7.37-7.29 (2H, m), 5.73 (1H, br s), 4.36-4.27 (1H, m), 3.95 (2H, dd, J 6.7, 8.4 Hz), 3.54 (2H, dd, J 6.1, 8.4 Hz). LCMS (ES$^+$) RT 2.84 minutes, pH 3 method, 506 (M+H)$^+$.

Example 14

(3R)-1-({2-[(2-Fluoro-4-iodophenyl)amino]thieno[2, 3-b]pyridin-3-yl}sulfonyl)pyrrolidin-3-ol Intermediate 7 (150 mg, 0.25 mmol) was dissolved in dichloromethane (6 mL), and triethylamine (75 µl, 0.50 mmol) and (R)-3-hydroxypyrrolidine (44 mg, 0.50 mmol) were added. The reaction mixture was stirred at ambient temperature under nitrogen for 18 hours. Dichloromethane (20 mL) was added and the solution washed with water (10 mL), dried (Na$_2$SO$_4$) and concentrated in vacuo. The residue was triturated with diethyl ether (10 mL), then washed with a further portion of diethyl ether (5 mL) to give the title compound as a white solid (80 mg, 63%). $\delta_H$ (DMSO-d$_6$) 9.08 (1H, br s), 8.33 (1H, d, J 3.4 Hz), 8.17-8.14 (1H, m), 7.84 (1H, dd, J 1.6, 9.9 Hz), 7.67 (1H, d, J 8.4 Hz), 7.49-7.39 (2H, m), 4.93 (1H, br s), 4.25-4.21 (1H, m), 3.41-3.34 (3H, m), 3.15-3.11 (1H, m), 1.93-1.71 (2H, m). LCMS (ES$^+$) RT 2.88 minutes, pH 3 method, 520 (M+H)$^+$.

Example 15 tert-Butyl-[1-({2-[(2-fluoro-4-iodophenyl)amino] thieno[2,3-b]pyridin-3-yl}sulfonyl)-azetidin-3-yl] carbamate Intermediate 7 (150 mg, 0.25 mmol) was dissolved in dichloromethane (6 mL), and triethylamine (75 µl, 0.50 mmol) and azetidin-3-ylcarbamic acid tert-butyl ester (86 mg, 0.50 mmol) were added. The reaction mixture was stirred at ambient temperature under nitrogen for 18 hours. Dichloromethane (20 mL) was added and the solution washed with water (10 mL), dried (Na$_2$SO$_4$) and concentrated in vacuo. The residue was triturated with diethyl ether (10 mL), then washed with a further portion of diethyl ether (5 mL) to give the title compound as a white solid (140 mg, 95%). $\delta_H$ (DMSO-d$_6$) 9.04 (1H, br s), 8.36 (1H, dd, J 1.5, 4.7 Hz), 8.09 (1H, dd, J 1.5, 8.2 Hz), 7.85 (1H, dd, J 1.9, 9.8 Hz), 7.70 (1H, dd, J 1.0, 8.4 Hz), 7.52-7.41 (3H, m), 4.22-4.19 (1H, m), 3.96 (2H, t, J 7.5 Hz), 3.63 (2H, t, J 7.5 Hz), 1.31 (9H, s). LCMS (ES$^+$) RT 3.48 minutes, pH3 method, 605 (M+H)$^+$.

Example 16

3-[(3-Aminoazetidin-1-yl)sulfonyl]-N-(2-fluoro-4-iodophenyl)thieno[2,3-b]pyridin-2-amine Example 15 (125 mg, 0.21 mmol) was dissolved in dichloromethane (3 mL). TFA (2 mL) was added and the reaction mixture was stirred at r.t. for 5 hours. After concentrating in vacuo, the residue was partitioned between ethyl acetate (100 mL) and sat. sodium carbonate solution (100 mL). The organic phase was dried (Na$_2$SO$_4$), and concentrated in vacuo to give the title compound as an off-white solid (65 mg, 63%). $\delta_H$ (DMSO-d$_6$) 8.33 (1H, dd, J 1.6, 4.7 Hz), 8.08 (1H, dd, J 1.6, 8.2 Hz), 7.83 (1H, dd, J 1.9, 9.9 Hz), 7.70-7.66 (1H, m), 7.50-7.39 (2H, m), 4.74 (3H, br s), 3.94-3.89 (2H, m), 3.64-3.55 (1H, m), 3.41-3.33 (2H, m). LCMS (ES$^+$) RT 2.67 minutes, pH 3 method, 505 (M+H)$^+$.

Example 17

2-[(2-Fluoro-4-iodophenyl)amino]thieno[2,3-b]pyridine-3-sulfonic acid

To a solution of Intermediate 6 (100 mg, 0.27 mmol) in DCM (5 mL), cooled in a CO$_2$/acetone bath, was added chlorosulfonic acid (184 µL, 2.7 mmol) dropwise. The reaction mixture was then placed in an ice bath and stirred for 30 minutes before N,N-di-isopropylethylamine (1.4 mL, 2.7 mmol) was added. The reaction mixture was stirred for 1 hour in the ice bath and then overnight at room temperature. The reaction mixture was diluted with DCM (25 mL) and NaHCO$_3$ solution (25 mL) added. The resulting precipitate was filtered off to give the title compound (49 mg, 40%). $\delta_H$ (DMSO-d$_6$) 9.95 (1H, s), 8.22 (1H, dd, J 1.6, 4.7 Hz), 8.11 (1H, dd, J 1.6, 8.1 Hz), 7.63, (1H, dd, J 1.8, 10.1 Hz), 7.49

(1H, d, J 8.6 Hz), 7.41 (1H, dd, J 8.6, 8.6 Hz), 7.30 (1H, dd, J 4.7, 8.1 Hz). LCMS (pH 3) RT 2.02 minutes, (ES$^+$) 451 (M+H)$^+$.

Example 18

1-{2-[(2-Fluoro-4-iodophenyl)amino]thieno[2,3-b]pyridin-3-yl}ethanone

To a solution of Intermediate 13 (300 mg, 1.76 mmol) in DMSO (5 mL) was added sodium hydride (77 mg, 60 wt % in oil, 1.93 mmol) and the mixture stirred at ambient temperature for 15 minutes. Intermediate 4 (516 mg, 1.85 mmol) was added and the mixture heated to 90° C. under nitrogen for 3 hours. The reaction was allowed to cool and was poured into ice/water (50 mL). The resultant beige precipitate was isolated by filtration and washed with a mixture of DCM-methanol to yield the title compound as a yellow crystalline solid (125 mg, 17%). $\delta_H$ (DMSO-d$_6$) 12.19 (1H, s), 8.35 (1H, d, J 3.5 Hz), 8.26 (1H, dd, J 8.3, 1.4 Hz), 7.86 (1H, dd, J 10.1, 1.8 Hz), 7.70 (1H, d, J 8.5 Hz), 7.61 (1H, dd, J 8.3, 4.7 Hz), 7.55 (1H, t, J 8.5 Hz), 2.69 (3H, s). LCMS (pH 3) RT 3.45 minutes, (ES$^+$) 413 (M+H)$^+$, (ES$^-$) 411 (M–H)$^-$.

Example 19

2-[(2-Fluoro-4-iodophenyl)amino]-N-[(trifluoromethyl)sulfonyl]thieno[2,3-b]pyridine-3-carboxamide EDC (93 mg, 0.48 mmol) was added to a solution of Intermediate 5 (100 mg, 0.24 mmol), 4-(dimethylamino)pyridine (177 mg, 1.45 mmol) and trifluoromethane-sulfonamide (72 mg, 0.48 mmol) in DMF (3 mL). The reaction mixture was stirred at r.t. for 20 h, then poured into EtOAc (25 mL). The organic solution was washed with 10% aq. HCl (2×25 mL) and sat. brine (25 mL). During the work-up the title compound precipitated in the organic layer; this was filtered off and washed with water, then EtOAc and hexanes, and dried under suction to give a yellow powder (28 mg, 21%). $\delta_H$ (DMSO-d$_6$) 12.06 (1H, s), 8.75-8.72 (1H, m), 8.29-8.27 (1H, m), 7.80-7.77 (1H, m), 7.65-7.63 (1H, m), 7.58-7.53 (2H, m), 7.39-7.35 (1H, m). LCMS RT 3.97 minutes, (ES$^-$) 544 (M–H)$^-$.

Example 20

N-(2-Fluoro-4-iodophenyl)-3-(1H-tetrazol-5-yl)thieno[2,3-b]pyridin-2-amine

To a solution of Intermediate 14 (300 mg, 0.76 mmol) in DMF (5 mL) was added sodium azide (60 mg, 0.91 mmol) and the mixture heated to 80° C. for 24 hours. The reaction was allowed to cool, poured into EtOAc (100 mL) and washed with saturated brine (3×100 mL). The organic phase was dried (Na$_2$SO$_4$), filtered and the volatiles removed in vacuo to give a crude residue which was azeotroped with heptane. Purification by column chromatography (SiO$_2$, 0-100% EtOAc in DCM) gave the title compound as a brown solid (120 mg, 36%). $\delta_H$ (DMSO-d$_6$) 9.91 (1H, s), 8.56 (1H, d, J 8.1 Hz), 8.44-8.42 (1H, m), 7.78 (1H, dd, J 10.4, 1.7 Hz), 7.60-7.57 (1H, m), 7.52-7.48 (1H, m), 7.41-7.38 (1H, m). One exchangeable proton was not observed. LCMS RT 2.27 minutes, (ES$^-$) 437 (M–H)$^-$, (ES$^+$) 439 (M+H)$^+$.

Example 21

N-(2-Fluoro-4-iodophenyl)-3-(5-methyl-1,3,4-oxadiazol-2-yl)thieno[2,3-b]pyridin-2-amine Intermediate 15 (64 mg, 0.14 mmol) was dissolved in POCl$_3$ (4 mL) and heated to 70° C. for 3 hours. After this time the reaction mixture was poured onto ice (50 mL) and extracted into DCM (50 mL). The organics were dried (Na$_2$SO$_4$) and evaporated in vacuo to give a brown residue. Purification by column chromatography (SiO$_2$, 50% EtOAc in DCM) gave the title compound (21 mg, 33%). $\delta_H$ (DMSO-d$_6$) 10.01 (1H, s), 8.40 (2H, m), 7.85 (1H, dd, J 1.5, 10.2 Hz), 7.67 (1H, d, J 8.6 Hz), 7.55-7.48 (2H, m), 2.63 (3H, s). LCMS (pH 3) RT 3.41 minutes, (ES$^+$) 453 (M+H)$^+$.

Example 22

N-(2-Fluoro-4-iodophenyl)-3-(5-phenyl-1,3,4-oxadiazol-2-yl)thieno[2,3-b]pyridin-2-amine Prepared from Intermediate 16 (70 mg, 0.13 mmol) by the method of Example 21 with POCl$_3$ (5 mL, 52 mmol) to give the title compound after column chromatography (50% DCM in hexanes) as a beige solid (25 mg, 37%). $\delta_H$ (DMSO-d$_6$) 10.17 (1H, s), 8.58 (1H, dd, J 1.5, 8.1 Hz), 8.44 (1H, dd, J 1.5, 4.7 Hz), 8.18 (2H, m), 7.87 (1H, dd, J 1.8, 10.1 Hz), 7.66 (4H, m), 7.55 (2H, m). LCMS (pH 10) RT 4.13 minutes, (ES$^+$) 515 (M+H)$^+$.

Example 23

[2-(2-Fluoro-4-iodo-phenylamino)-thieno[2,3-b]pyridin-3-yl]-(pyridin-4-yl)-methanone Intermediate 19 (0.25 g, 1.05 mmol) in DMSO (5 mL) was treated under nitrogen with NaH (50 mg, 1.19 mmol) and stirred at room temperature for 20 minutes. Intermediate 4 (315 mg, 1.13 mmol) was added and the reaction heated at 90° C. for 3 h. The reaction mixture was quenched with water, extracted into DCM, dried (sodium sulphate), filtered, concentrated in vacuo and chromatographed on silica with DCM/ethyl acetate (1-100%) to give the title compound (95 mg). $\delta_H$ (DMSO-d$_6$) 11.42 (1H, s), 8.77 (2H, d, J 4.5 Hz), 8.31-8.29 (1H, m), 7.85 (1H, d, J 10.1 Hz), 7.69 (1H, d, J 8.8 Hz), 7.56-7.51 (3H, m), 7.23-7.19 (1H, m), 6.99 (1H, d, J 8.7 Hz). LCMS (pH 10) RT 3.17 minutes, (ES$^+$) 476 (M+H)$^+$.

Example 24

[2-(2-Fluoro-4-iodophenylamino)thieno[2,3-b]pyridin-3-yl]-(pyrrolidin-2-yl)-methanone Intermediate 24 (150 mg, 0.26 mmol) in 1,4-dioxane (1 mL) was treated with 4M HCl in 1,4-dioxane (3 mL) and stirred at room temperature for 30 minutes. The solvent was removed in vacuo and the residue triturated with diethyl ether to give the title compound (125 mg). $\delta_H$ (DMSO-d$_6$) 11.82 (1H, s), 9.73 (1H, br s), 8.85 (1H, br s), 8.41 (1H, d, J 4.7 Hz), 8.18 (1H, d, J 8.3 Hz), 7.92 (1H, d, J 9.9 Hz), 7.75 (1H, d, J 8.5 Hz), 7.58 (1H, t, J 8.4 Hz), 7.51 (1H, dd, J 8.3, 4.7 Hz), 5.21 (1H, br s), 4.25-3.95 (2H, m), 3.49-3.36 (1H, m), 3.35-3.21 (1H, m), 2.12-1.80 (2H, m). LCMS (pH 3) RT 1.72 minutes, (ES$^+$) 468 (M+H)$^+$.

Example 25

[2-(2-Fluoro-4-iodophenylamino)thieno[2,3-b]pyridin-3-yl]-(piperidin-4-yl)-methanone Intermediate 28 (290 mg, 0.60 mmol) was dissolved in TFA (3 mL) and stirred at room temperature for 30 minutes. The solution was then warmed to 50° C. for 3 h. The reaction was concentrated in vacuo, azeotroped with heptane, redissolved in DCM, washed with sodium hydrogencarbonate solution, dried (sodium sulphate), filtered and concentrated in vacuo. Trituration with diethyl ether followed by preparative HPLC (pH=10) gave the title compound (47 mg). $\delta_H$ (DMSO-$d_6$) 8.51 (1H, dd, J 8.0, 1.6 Hz), 9.98 (1H, br s), 7.81 (1H, dd, J 4.7, 1.4 Hz), 7.48 (1H, dd, J 10.3, 1.9 Hz), 7.39 (1H, dd, J 8.4, 1.4 Hz), 7.02 (1H, t, J 8.7 Hz), 6.95 (1H, dd, J 8.0, 4.7 Hz), 4.07-3.90 (1H, m), 3.50-3.10 (3H, br m), 2.88-2.71 (2H, m), 2.01-1.92 (2H, m), 1.78-1.60 (2H, m). LCMS (pH 3) RT 1.81 minutes, (ES$^+$) 482 (M+H)$^+$.

Example 26

(Azetidin-3-yl)-[2-(2-fluoro-4-iodophenylamino)thieno[2,3-b]pyridin-3-yl]-methanone Intermediate 32 (80 mg, 0.14 mmol) in DCM (3 mL) was treated with TFA (1 mL) and stirred at room temperature for 1 h. The reaction mixture was concentrated in vacuo and the residue azeotroped with toluene. The resulting solid was triturated with diethyl ether, dissolved in DCM, washed with sodium hydrogencarbonate solution, dried (sodium sulphate), filtered, concentrated and freeze dried from methanol-water to give the title compound (45 mg). $\delta_H$ (DMSO-$d_6$) 8.46 (1H, dd, J 8.1, 1.7 Hz), 8.29 (1H, dd, J 4.7, 1.7 Hz), 7.97 (1H, dd, J 10.2, 1.9 Hz), 7.78 (1H, ddd, J 8.3, 1.9, 0.9 Hz), 7.56 (1H, t, J 8.3 Hz), 7.39 (1H, dd, J 7.9, 4.7 Hz), 4.23-4.08 (2H, m), 3.00-2.92 (1H, m), 2.86-2.76 (1H, m), 2.75-2.65 (1H, m), 1.68 (2H, br m). LCMS (pH 3) RT 1.73 minutes, (ES$^+$) 454 (M+H)$^+$.

Example 27

3-({1-[2-(2-Fluoro-4-iodophenylamino)thieno[2,3-b]pyridine-3-sulfonyl]azetidin-3-ylmethyl}amino)propionic acid Example 11 (67 mg, 0.108 mmol) in MeOH (5 mL) was treated with 2M sodium hydroxide solution (1 mL, 2.0 mmol). The reaction mixture was stirred for 18 h at room temperature before dilution with water (5 mL) and removal of volatiles in vacuo. Following addition of 2M hydrochloric acid (~1 mL) the resultant precipitate was filtered off and washed with water (25 mL) to afford the title compound as a white solid (41 mg, 70%). $\delta_H$ (DMSO-$d_6$) 8.29 (1H, d J 3.9 Hz), 8.07 (1H, m), 7.80 (1H, m), 7.65 (1H, m), 7.40 (2H, m), 3.89 (2H, t, J 7.8 Hz), 3.55 (2H, m), 2.63 (5H, m), 2.20 (2H, t, J 6.6 Hz). LCMS (pH 10) RT 2.10 minutes, (ES$^+$) 591 (M+H)$^+$.

When ranges are used herein, for example, for biological activity, such as binding data, chemical properties, such as chemical formulae, or dosage ranges, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A compound of formula (I), or a pharmaceutically acceptable salt or N-oxide thereof:

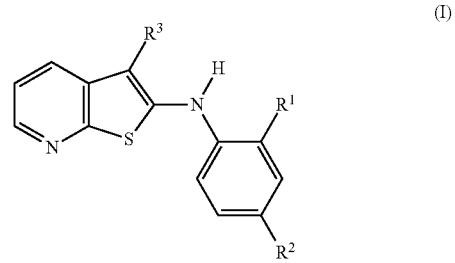

wherein
$R^1$ is hydrogen, halogen, or $C_{1-6}$ alkyl;
$R^2$ is halogen or $C_{1-6}$ alkyl;
$R^3$ is —SO$_2$NR$^b$R$^c$; and
$R^b$ and $R^c$, when taken together with the nitrogen atom to which they are both attached, form a heterocyclic ring selected from optionally substituted azetidinyl, optionally substituted pyrrolidinyl, optionally substituted piperidinyl, optionally substituted morpholinyl, optionally substituted thiomorpholinyl, optionally substituted piperazinyl, optionally substituted homopiperidinyl, optionally substituted homomorpholinyl and optionally substituted homopiperazinyl;
wherein the one or more optional substituents are each independently selected from the group consisting of:
$C_{1-6}$ alkyl, hydroxy, hydroxy($C_{1-6}$)alkyl, $C_{1-6}$ alkoxy, $C_{1-6}$ alkoxy($C_{1-6}$)alkyl, amino($C_{1-6}$)alkyl, (amino)(hydroxy)($C_{1-6}$)alkyl, halogen, oxo, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, di($C_{1-6}$)alkylhydrazinylcarbonyl, amino, $C_{1-6}$ alkylamino, di($C_{1-6}$)alkylamino, $C_{2-6}$ alkylcarbonylamino, $C_{2-6}$ alkoxycarbonylamino, $C_{2-6}$ alkoxycarbonylamino($C_{1-6}$)alkyl, $C_{2-6}$ alkoxycarbonyl-($C_{1-6}$)alkylamino($C_{1-6}$)alkyl, aminocarbonylamino, aminocarbonyl, $C_{1-6}$ alkylamino-carbonyl, di($C_{1-6}$)alkylaminocarbonyl, aminosulfonyl, $C_{1-6}$ alkylsulfonyl and $C_{1-6}$ alkylaminocarbonyl($C_{1-6}$)alkyl.

2. A compound according to claim 1, wherein R$^b$ and R$^c$ are taken together with the nitrogen atom to which they are attached to form a cyclic group selected from optionally substituted azetidin-1-yl, optionally substituted pyrrolidin-1-yl and optionally substituted piperidin-1-yl.

3. A compound according to claim 1 wherein the cyclic group formed by R$^b$ and R$^c$ and the nitrogen atom to which they are attached is optionally substituted with one or more of hydroxy, amino, amino($C_{1-6}$)alkyl, $C_{2-6}$ alkoxycarbonylamino, carboxy($C_{1-6}$)alkylamino ($C_{1-6}$)alkyl or $C_{2-6}$ alkoxycarbonyl($C_{1-6}$)alkylamino($C_{1-6}$)alkyl.

4. A compound according to claim 3 wherein the cyclic group formed by R$^b$ and R$^c$ and the nitrogen atom to which they are attached is substituted with hydroxy, amino, amino ($C_{1-6}$)alkyl, $C_{2-6}$ alkoxycarbonylamino, carboxy($C_{1-6}$)alkylamino($C_{1-6}$)alkyl or $C_{2-6}$ alkoxycarbonyl($C_{1-6}$)alkylamino ($C_{1-6}$)alkyl.

5. A compound or a pharmaceutically acceptable salt or N-oxide thereof according to claim 1, having the following formula (II):

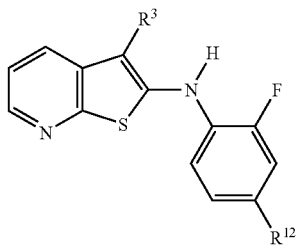

(II)

wherein:
R$^{12}$ is halogen.

6. A compound according to claim 5, wherein R$^{12}$ is bromo or iodo.

7. A compound or a pharmaceutically acceptable salt or N-oxide thereof according to claim 1, which is selected from the group consisting of:
- N-(2-Fluoro-4-iodophenyl)-3-(pyrrolidin-1-ylsulfonyl) thieno[2,3-b]pyridin-2-amine;
- 3-{[3-(Aminomethyl)azetidin-1-yl]sulfonyl}-N-(2-fluoro-4-iodophenyl)thieno-[2,3-b]pyridin-2-amine;
- tert-Butyl [(3R)-1-({2-[(2-fluoro-4-iodophenyl)amino]thieno[2,3-b]pyridin-3-yl}sulfonyl)pyrrolidin-3-yl]carbamate;
- 3-{[(3R)-3-Aminopyrrolidin-1-yl]sulfonyl}-N-(2-fluoro-4-iodophenyl)thieno[2,3-b]pyridin-2-amine;
- tert-Butyl [(3S)-1-({2-[(2-fluoro-4-iodophenyl)amino]thieno[2,3-b]pyridin-3-yl}sulfonyl)pyrrolidin-3-yl]carbamate;
- 3-{[(3S)-3-Aminopyrrolidin-1-yl]sulfonyl}-N-(2-fluoro-4-iodophenyl)thieno[2,3-b]pyridin-2-amine;
- N-(2-Fluoro-4-iodophenyl)-3-(piperazin-1-ylsulfonyl)thieno[2,3-b]pyridin-2-amine hydrochloride;
- 3-(Aminomethyl)-1-({2-[(2-fluoro-4-iodophenyl)amino]thieno[2,3-b]pyridin-3-yl}sulfonyl)azetidin-3-ol;
- Ethyl N-{[1-({2-[(2-fluoro-4-iodophenyl)amino]thieno[2,3-b]pyridin-3-yl}sulfonyl)azetidin-3-yl]methyl}-beta-alaninate;
- Ethyl N-{[1-({2-[(2-fluoro-4-iodophenyl)amino]thieno[2,3-b]pyridin-3-yl}sulfonyl)azetidin-3-yl]methyl}glycinate;
- 1-({2-[(2-Fluoro-4-iodophenyl)amino]thieno[2,3-b]pyridin-3-yl}sulfonyl)-azetidin-3-ol;
- (3R)-1-({2-[(2-Fluoro-4-iodophenyl)amino]thieno[2,3-b]pyridin-3-yl}sulfonyl)-pyrrolidin-3-ol;
- tert-Butyl-[1-({2-[(2-fluoro-4-iodophenyl)amino]thieno[2,3-b]pyridin-3-yl}sulfonyl)azetidin-3-yl]carbamate;
- 3-[(3-Aminoazetidin-1-yl)sulfonyl]-N-(2-fluoro-4-iodophenyl)thieno[2,3-b]pyridin-2-amine; and
- 3-({1-[2-(2-Fluoro-4-iodophenylamino)thieno[2,3-b]pyridine-3-sulfonyl]azetidin-3-ylmethyl}amino)propionic acid.

8. A pharmaceutical composition comprising a compound or a pharmaceutically acceptable salt or N-oxide thereof according to claim 1, in combination with a pharmaceutically acceptable carrier.

* * * * *